(12) United States Patent
Cai

(10) Patent No.: US 9,050,298 B2
(45) Date of Patent: Jun. 9, 2015

(54) METHOD OF TREATING ISCHEMIA/REPERFUSION INJURIES TO A HEART WITH NETRIN-1

(75) Inventor: Hua Cai, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 142 days.

(21) Appl. No.: 13/698,541

(22) PCT Filed: May 27, 2011

(86) PCT No.: PCT/US2011/038277
§ 371 (c)(1),
(2), (4) Date: Nov. 16, 2012

(87) PCT Pub. No.: WO2011/150299
PCT Pub. Date: Dec. 1, 2011

(65) Prior Publication Data
US 2013/0157944 A1    Jun. 20, 2013

Related U.S. Application Data

(60) Provisional application No. 61/349,572, filed on May 28, 2010.

(51) Int. Cl.
| | |
|---|---|
| *C07K 14/435* | (2006.01) |
| *A61K 38/16* | (2006.01) |
| *A61K 38/17* | (2006.01) |
| *A61K 38/18* | (2006.01) |
| *A61K 31/519* | (2006.01) |
| *A61K 31/7105* | (2006.01) |
| *C07K 14/475* | (2006.01) |
| *C12N 5/077* | (2010.01) |
| *C12N 5/071* | (2010.01) |
| *A61K 38/00* | (2006.01) |

(52) U.S. Cl.
CPC .............. *A61K 38/18* (2013.01); *A61K 31/519* (2013.01); *A61K 31/7105* (2013.01); *C07K 14/475* (2013.01); *A61K 38/00* (2013.01); *C12N 5/0657* (2013.01); *C12N 5/0691* (2013.01); *C12N 5/0692* (2013.01)

(58) Field of Classification Search
None
See application file for complete search history.

(56) References Cited

U.S. PATENT DOCUMENTS

2006/0153840 A1 * 7/2006 Eichmann et al. ......... 424/143.1
2010/0040622 A1   2/2010 Li

FOREIGN PATENT DOCUMENTS

| CA | 2638974 A1 | 9/2007 |
| WO | 2006054000 A2 | 5/2006 |

OTHER PUBLICATIONS

International Search Report and Written Opinion received in PCT/US2011/038277, mailed Feb. 9, 2012.
Zhang, J. et al. (2010) "Netrin-1 Prevents Ischemia/Reperfusion-induced Myocardial Infarction via a DCC/ERK1/2/eNOSs1177/NO/DCC Feed-forward Mechanism" J. of Molecular and Cellular Cardiology, 48:1060-1070.

* cited by examiner

Primary Examiner — Christine J Saoud
Assistant Examiner — Jon M Lockard
(74) Attorney, Agent, or Firm — Suzannah K. Sundby, Esq.; Canady + Lortz LLP

(57) ABSTRACT

Disclosed herein are methods for treating, inhibiting, or reducing ischemia/reperfusion injury of a cardiac tissue; increasing phosphorylation of ERK1/2 and/or eNOS in a cardiac tissue; treating, inhibiting, or reducing loss of NO; treating, inhibiting, or reducing uncoupling of NOS; increasing recoupling of NOS; treating, inhibiting, or reducing loss of DCC protein and mRNA expression in a cardiac tissue; decreasing or reducing the infarct size of a heart resulting from ischemia/reperfusion injury; decreasing or reducing superoxide production by a cardiac tissue caused by ischemia/reperfusion injury; treating, inhibiting, or reducing neointimal formation and restenosis; treating, inhibiting, or reducing apoptosis of mobilized endothelial progenitor cells; or a combination thereof of a blood vessel (such as an artery, a coronary artery, a vein, or a capillary) or a portion of the blood vessel in a subject which comprise the administration of netrin-1.

19 Claims, 25 Drawing Sheets

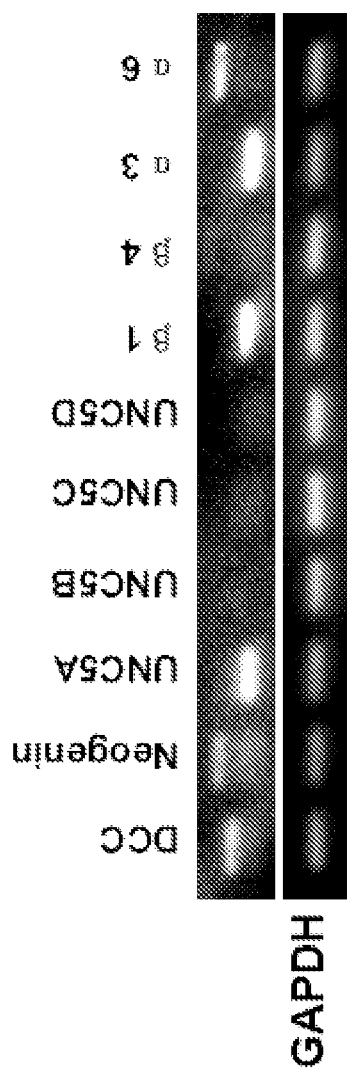
Figure 1A
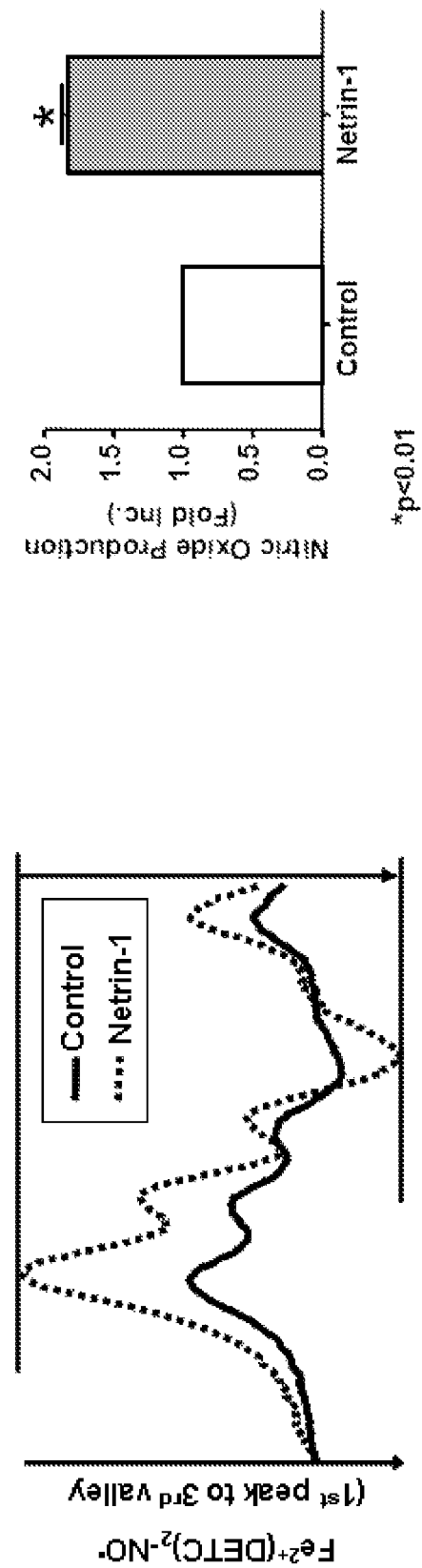
Figure 1C
Figure 1B

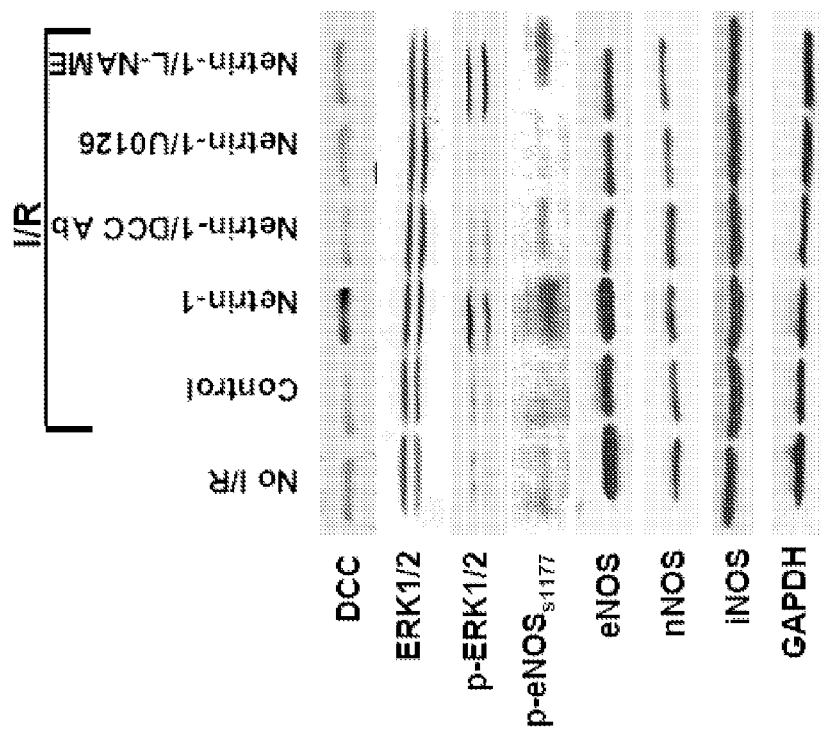
Figure 5A
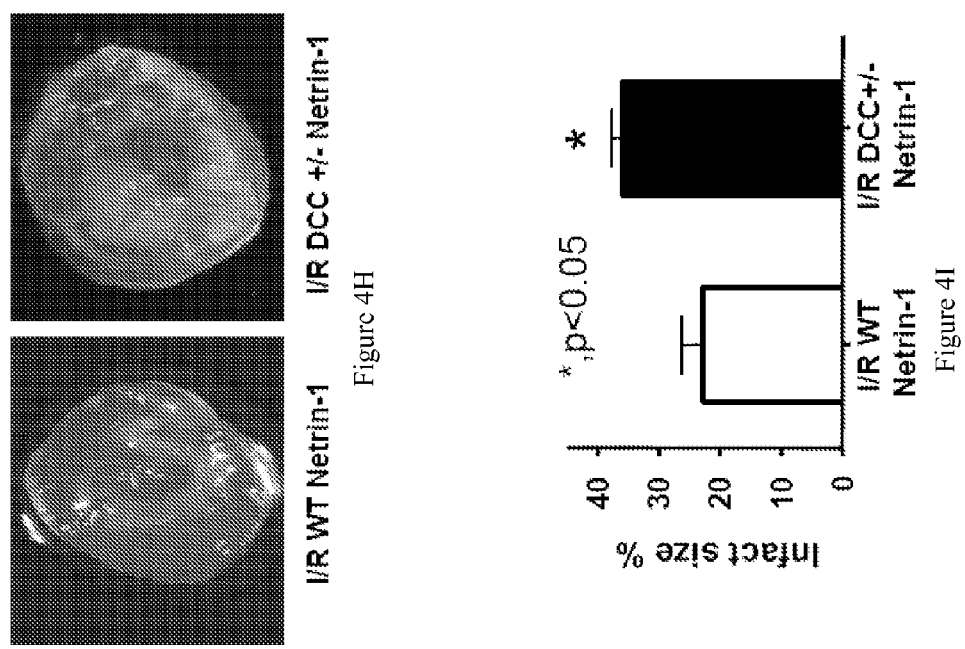
Figure 4H
Figure 4I

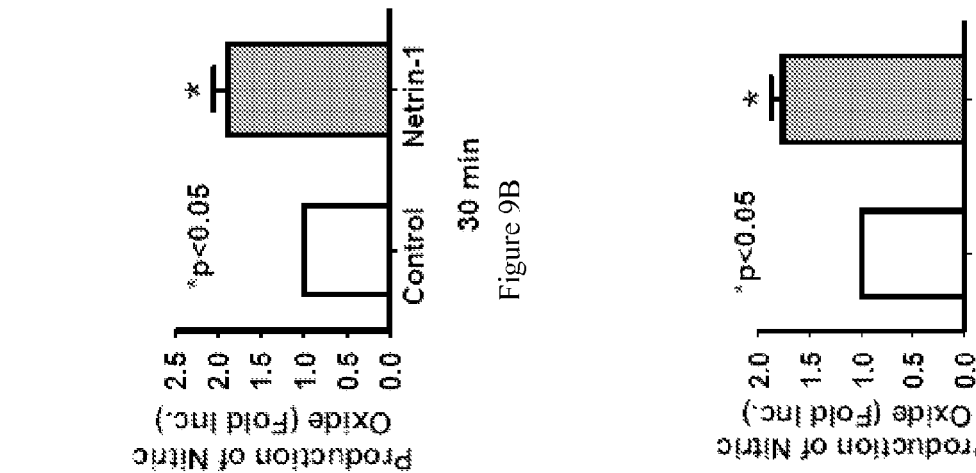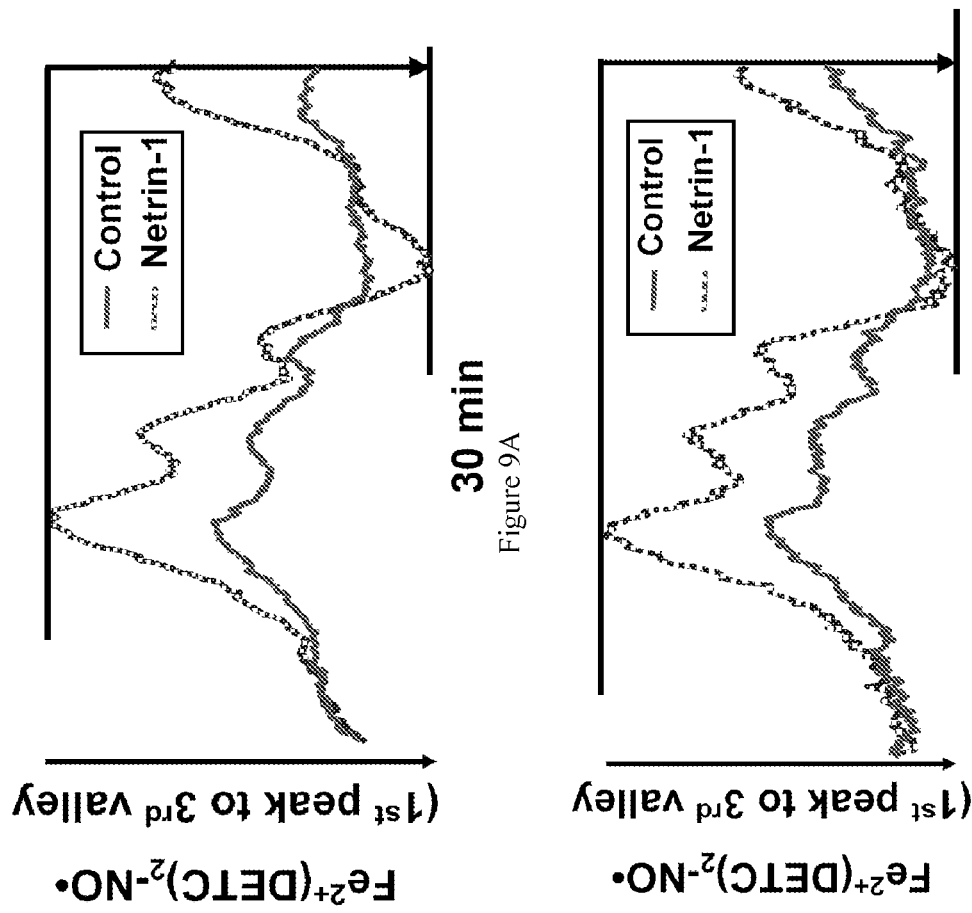

* P=0.001 compared against all others

* P<0.001 compared with no I/R and I/R netrin-1

# P<0.001 compared with no I/R and I/R

* P<0.001 compared with no L-NAME

# P<0.001 compared with No I/R control and I/R Netrin-1 s P=0.006 compared with no I/R and I/R Sepi.

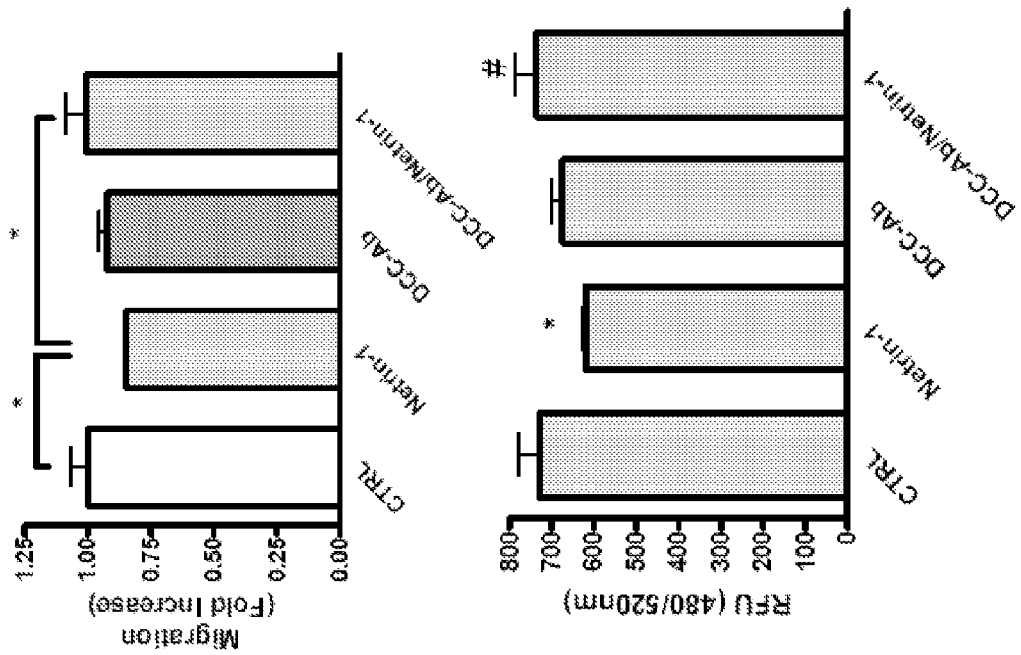
Figure 24
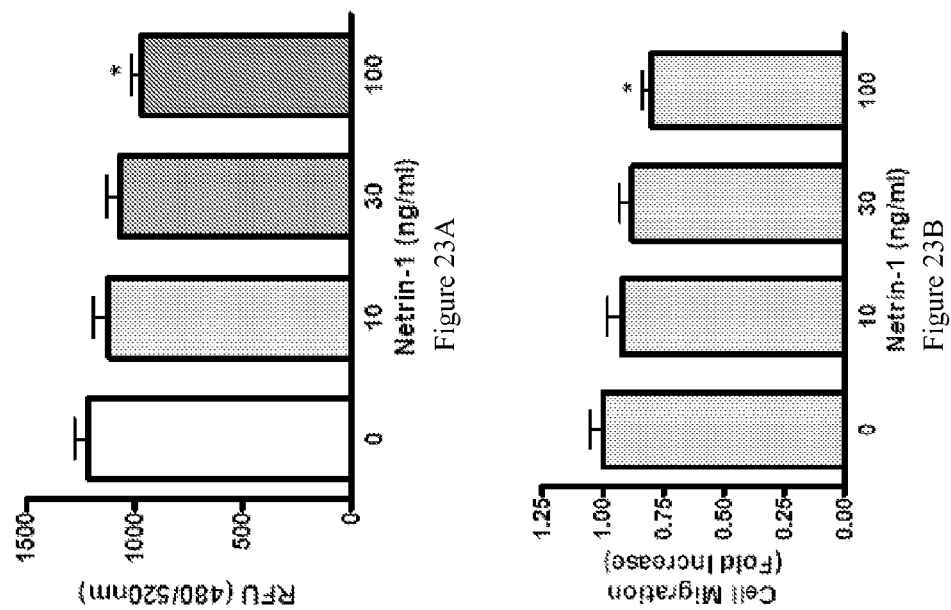
Figure 23A
Figure 23B

METHOD OF TREATING ISCHEMIA/REPERFUSION INJURIES TO A HEART WITH NETRIN-1

CROSS-REFERENCE TO RELATED APPLICATIONS

This application is a U.S. National phase of PCT/US2011/038277 and claims the benefit of U.S. Patent Application Ser. No. 61/349,572, filed 28 May 2010, both of which are herein incorporated by reference in their entirety.

REFERENCE TO A SEQUENCE LISTING SUBMITTED VIA EFS-WEB

The content of the ASCII text file of the sequence listing named "20110523_034044_088WO1_seq_ST25" which is 4.1 KB in size was created on 23 May 2011 and electronically submitted via EFS-Web herewith the application is incorporated herein by reference in its entirety.

BACKGROUND OF THE INVENTION

1. Field of the Invention

The present invention relates to netrin-1, compositions thereof, and methods of treatment employing netrin-1.

2. Description of the Related Art

Netrin-1 is a secreted molecule that is largely known to play a defined role in guiding vertebrate commissural axons in neuronal development. See Kennedy et al. (1994) Cell 78:425-35; Serafini et al. (1994) Cell 78:409-24; and Serafini et al. (1996) Cell 87:1001-14. Recent studies have further demonstrated a critical role of netrin-1 in endothelial cell proliferation, migration and angiogenic signaling, in addition to morphogenesis of epithelial cells. See Park et al. (2004) PNAS USA 101:16210-5; Lu et al. (2004) Nature 432:179-86; Carmeliet et al. (2005) Nature 436:193-200; Nguyen et al. (2006) PNAS USA 103:6530-5; Wilson et al. (2006) Science 313:640-4; Navankasattusas et al. (2008) Development 135:659-67; Liu et al. (2004) Curr Biol 14:897-905; and Nikolopoulos et al. (2005) Cell Cycle 4:e131-5. At least eight netrin receptors have been characterized in neurons, vascular system and other cell types in mammals. These include deleted in colorectal cancer (DCC), UNC5A, B, C, D, neogenin, a6β4 and α3β1 integrins. See Tessier-Lavigne et al. (1996) Science 274:1123-33; Huber et al. (2003) Annu Rev Neurosci 26:509-63; Cirulli et al. (2007) Nat Rev Mol Cell Biol 8:296-306; and Yebra et al. (2003) Dev Cell 5:695-707. Netrin-1 binding to DCC mediates attractive outgrowth of axons, as well as positive angiogenic signalings in endothelial and vascular smooth muscle cells. In contrast, the UNC5B receptor appears repulsive, mediating cellular effects such as filopodial retraction, particularly in developing capillaries. See Lu et al. (2004) Nature 432:179-86; and Larrivee et al. (2007) Genes Dev 21:2433-47.

In a recent study it was found that netrin-1 induces production of nitric oxide (NO) to promote aortic endothelial cell migration and proliferation. See Nguyen et al. (2006) PNAS USA 103:6530-5. It was also found that netrin-1 induced NO production is DCC-dependent, involving a feed-forward activation of ERK1/2-eNOS. Binding of netrin-1 to DCC leads to an initial activation of ERK1/2, consequent phosphorylation and activation of eNOS as well as production of NO, which in turn further activates ERK1/2 and more NO production to prompt endothelial cell growth and migration. It has been established that a deficiency in endothelial nitric oxide synthase (eNOS) exacerbates myocardial I/R injury, whereby eNOS overexpression, NO donor, or dietary supplementation of nitrite significantly improved cardiac function in models of hypoxia and myocardial I/R injury, however with unclear molecular mechanisms. See Elrod et al. (2006) Arterioscler Thromb Vasc Biol 26:1517-23; Jones et al. (2004) Am J Physiol Heart Circ Physiol 286:H276-82; Pabla et al. (1996) Circ Res 78:65-72; Siegfried et al. (1992) Am J Physiol 263:H771-7; and Hataishi et al. (2006) Am J Physiol Heart Circ Physiol 291:H379-84. In addition, netrin-1 has been shown to protect against renal I/R injury in vivo, with unknown molecular/signaling mechanisms. See Wang et al. (2008) Am J Physiol Renal Physiol 294(4):F739-47. However, the overall expression profile of netrin-1 receptors in the heart has remained completely unknown; and that the effects and molecular mechanisms of netrin-1 on cardioprotection during I/R, and practical treatment methods for such, has never been explored previously.

SUMMARY OF THE INVENTION

The present invention provides methods and compositions for treating, inhibiting, or reducing ischemia/reperfusion injury of a cardiac tissue; increasing phosphorylation of ERK1/2 and/or eNOS in a cardiac tissue; treating, inhibiting, or reducing loss of NO in a cardiac tissue; or reducing loss of DCC protein and mRNA expression in a cardiac tissue; or reducing loss of eNOS protein expression in a cardiac tissue decreasing; or reducing the infarct size of a heart resulting from ischemia/reperfusion injury; or decreasing or reducing superoxide production by a cardiac tissue caused by ischemia/reperfusion injury; or treating, inhibiting, or reducing NOX4 upregulation caused by ischemia/reperfusion injury; or treating, inhibiting, or reducing NOS uncoupling caused by ischemia/reperfusion injury; or increasing NOS recoupling in a cardiac tissue; or treating, inhibiting, or reducing mitochondrial damage caused by ischemia/reperfusion injury; or treating, inhibiting, or reducing neointimal formation and restenosis; or treating, inhibiting, or reducing vascular smooth muscle cell migration and proliferation; or increasing DCC activation in vascular smooth muscle cells; or treating, inhibiting, or reducing apoptosis of endothelial progenitor cells; or a combination thereof of a blood vessel (such as an artery, a coronary artery, a vein, or a capillary) or a portion of the blood vessel in a subject, preferably a mammalian subject, more preferably a human subject, which methods and compositions employ netrin-1, preferably in a therapeutically effective amount.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 1A is a picture of a Western blot showing the expression of Netrin-1 receptors in the heart. Whole mouse hearts (C57BL/6J) were homogenated for RNA and protein extraction. Expression of DCC, neogenin, UNC5A-D, integrin β1, β4, α3, and α6 mRNA in the mouse heart was measured by RT-PCR and normalized to levels of GAPDH. FIG. 1B shows representative electron spin resonance (ESR) spectra. Mouse hearts were freshly isolated and perfused with netrin-1 (100 ng/ml) on the Langendorff rig for 120 min. Hearts were then homogenated and incubated with the NO-specific spin trap $Fe^{2+}(DETC)_2$ for 60 min prior to ESR analysis of NO production. FIG. 1C is a graph providing grouped data of netrin-1 stimulated cardiac nitric oxide (NO) production from six independent experiments (Means±SEM, n=6), *p<0.01.

FIG. 4H provides representative TTC stains of netrin-1 perfused, IR-ed hearts from WT or DCC +/−mice. Color photographs of this figure are provided in Zhang & Cai (2010) J Molecular and Cellular Cardiology 48:1060-70, which is herein incorporated by reference. FIG. 4I provides infarct size shown in quantitative grouped data of FIG. 4H (Means±SEM, n=3), *p<0.05.

FIG. 5A are representative Western blots which evidence the DCC-ERK1/2-eNOS$_{1177}$-NO-DCC feed-forward loop mechanism upon netrin-1 activation. Hearts were perfused as described in FIG. 4A. All quantitative data are expressed in Means±SEM for statistical analysis.

FIGS. 9A-9F evidence that netrin-1 stimulates NO production from primarily isolated cardiomyocytes. Cardiomyocytes were exposed to netrin-1 (100 ng/ml) and harvested at 30 min and 60 min for analysis of NO production, DCC expression and ERK1/2 activation. FIGS. 9A-9D show representative ESR spectra and grouped data for NO production from three independent experiments. *p<0.05 vs control. FIG. 9E are Western blots of DCC expression and ERK1/2 phosphorylation. FIG. 9F is a representative image of freshly isolated cardiomyocytes.

FIG. 11A diagrammatically provides the experimental protocols of I/R and netrin-1 treatment. FIG. 11B shows the superoxide production from heart homogenates after the Langendorff experiments (n=3 for all groups). Superoxide levels were measured using electron spin resonance (ESR), and found significantly higher under I/R than all other conditions (p=0.001, ANOVA with Holm-Sidak post-hoc test). Netrin-1 completely attenuated FR-induced superoxide production.

FIG. 14A provides data from Western analysis of hearts isolated from mice treated with NOX4 siRNA indicating successful silencing of NOX4 protein expression by siRNA. The top panel shows a representative Western blot of NOX4 expression. The middle panel shows actin loading control, and the bottom panel shows summarized data. FIG. 14B shows that NOX4 siRNA markedly reduced infarct size. Infarct size was analyzed by TTC staining FIG. 14C shows L-NAME sensitive superoxide measurements from heart homogenates. Summarized data shows that while superoxide levels were increased in NOX4 siRNA treated hearts compared to controls, NOS coupling state was restored in the I/R condition when NOX4 levels were inhibited by siRNA treatment. FIG. 14D provides results of the mitochondria swelling assay using freshly prepared mitochondria. Summarized data indicate that mitochondrial function was improved in I/R hearts treated with NOX4 siRNA when compared with control siRNA treated hearts.

FIG. 15A shows that sepiapterin perfusion recouples NOS (n=4 each). Superoxide levels measured used ESR, with and without the addition of L-NAME to assess the coupling state of NOS. Multiple comparisons made with ANOVA with Holm-Sidak post hoc test (P<0.001). FIG. 15B shows data from a mitochondria swelling assay that was used to assess mitochondrial function (n=4 each group). Increased swelling was observed in mitochondria isolated from I/R hearts (▲A) compared to no I/R (■) and I/R perfused with sepiapterin (▼) (P=0.006, ANOVA with Holm-Sidak, data at 12 min). Sepiapterin treatment effectively diminished mitochondrial dysfunction.

Figure 21:
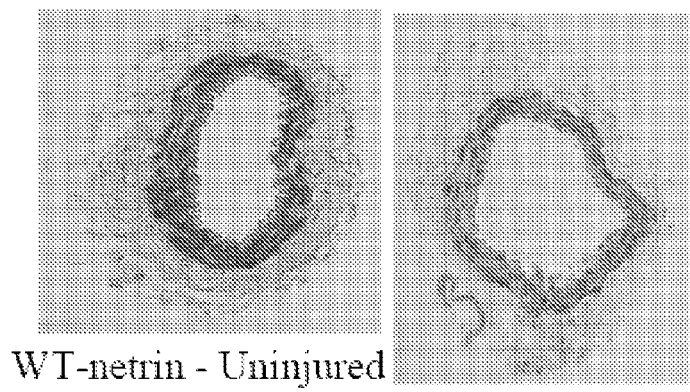
FIG. 21 shows micrographs of blood vessel sections of femoral arteries in netrin-1 treated mice. Mice were pretreated with netrin-1 at 15 ng/day for 2 days prior to wire injury of one femoral artery. The netrin-1 treatment was continued through 14 days using controlled release osmotic minipumps. The other un-injured femoral artery from the same mouse serves as a control. In the presence of netrin-1 treatment, injury did not induce any observable neointimal formation, as the inner layer of the vessel had the same thickness. The neointimal formation is an important process of restenosis in coronary arteries post PTCA treatment of acute myocardial infarction.
Figure 22:
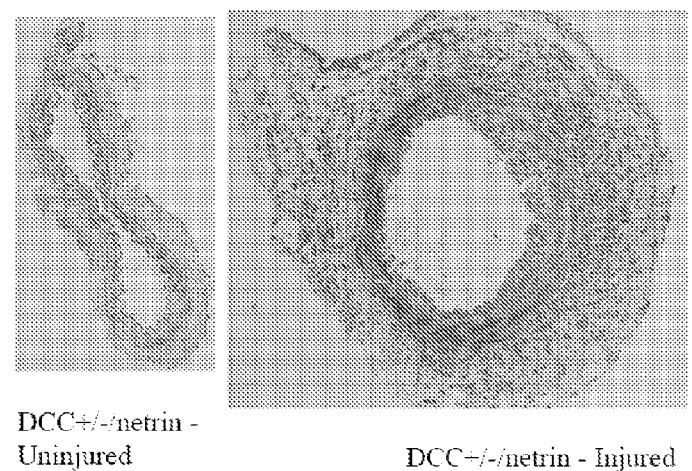

FIG. 22 shows micrographs of blood vessel sections of femoral arteries in netrin-1 treated DCC +/−mice. The treatment conditions were the same as described for FIG. 21. As is obvious, netrin-1 induced protection of neointimal formation was lost in DCC +/−mice. The injured femoral artery from the DCC +/−mouse suffered from neointimal formation despite of netrin-1 treatment.

FIG. 23A netrin-1 dose-dependently inhibits vascular smooth muscle cell (VSMC) proliferation. Confluent rat aortic smooth muscle cells (RASMC) were treated with different concentrations of netrin-1 (10, 30, 100 ng/ml) prior to being subjected to BrdU proliferation assay.

FIG. 23B shows netrin-1 dose-dependently inhibits vascular smooth muscle cell (VSMC) migration. RASMC were identically treated as in FIG. 24A above and then subjected to transwell migration assay. These VSMC proliferation and migration responses are hallmarks of neointimal formation and restenosis.

FIG. 24 shows the inhibitory effects of netrin-1 on vascular smooth muscle migration and proliferation were attenuated by DCC-antibody. DCC-antibody was used to pre-treat the cells for 30 min prior to addition of netrin-1 (100 ng/ml). The proliferation and migration assays were performed as described above.

Figure 25A:
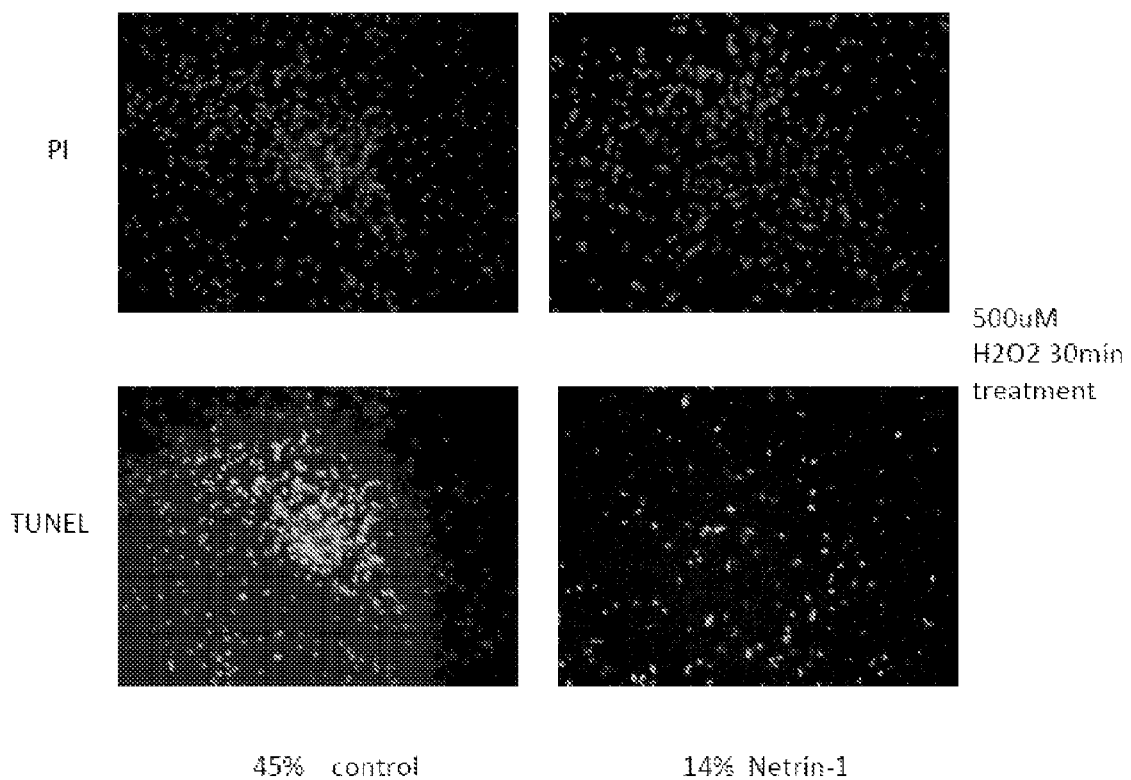
Figure 25B:
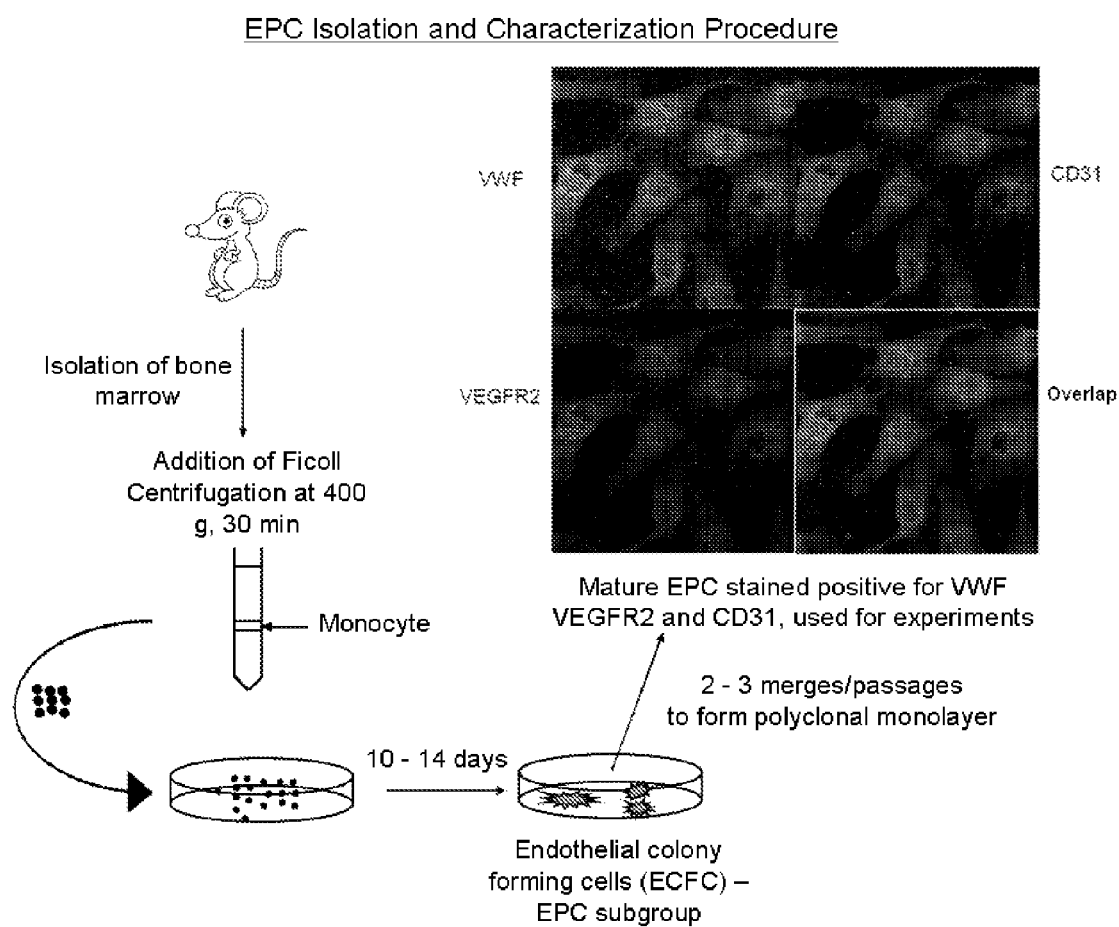

FIG. 25A shows mobilized endothelial progenitor cells (EPCs) were significantly protected by netrin-1 from reactive oxygen species-induced apoptosis. EPCs have important roles in injury-induced vascular repair, and hence relevant to post procedure management of PTCA treatment of acute myocardial infarction. FIG. 25B schematically shows the protocol, i.e. bone marrow (BM)-derived EPCs were isolated, cultured and characterized as illustrated. These cells were then pre-treated with netrin-1 (100 ng/ml) prior to exposure to hydrogen peroxide (levels elevated during injury and known to destabilize EPC) and determination of apoptosis. As clearly shown in the figure, the control EPCs had 45% apoptotic cells after hydrogen peroxide treatment while this was markedly attenuated to 14% by netrin-1 treatment.

DETAILED DESCRIPTION OF THE INVENTION

Netrins and their receptors are well known in the art, as exemplified in U.S. Pat. Nos. 5,565,331; 6,096,866; 6,017,714; 6,309,638; and 6,670,451; and in US20060019896 and US20060025335, which are herein incorporated by reference.

The present invention is directed to netrin-1 and therapeutic treatments comprising the administration of netrin-1. As used herein, "netrin-1" refers to any netrin-1 protein, including human netrin-1 protein and mouse netrin-1 protein and variants thereof as set forth in US 20100183520, which is herein incorporated by reference.

The present invention is directed to treating, inhibiting, or reducing ischemia/reperfusion injury to cardiac tissue in a subject. As used herein, the term "ischemia/reperfusion injury" (I/R injury) refers to an injury of an organ, e.g. heart, caused by putting the organ into an ischemic condition such as by thomboembolic events, surgery or cardiac standstill. Clinically relevant situations include occlusion of coronary arteries/branches that happen during myocardial infarction (ischemia). Treatment with percutaneous transluminal coronary angioplasty (PTCA) procedure creates a reperfusion condition that is known to cause additional injury that can be however protected by pharmacological post-conditioning (administering netrin-1 at the reperfusion stage). Therefore this invention is also directed towards acute treatment of myocardial infarction by administering netrin-1 (e.g. intravenously) alone or in combination with PTCA/drug eluting stent.

1. Netrin-1 Induces Cardioprotection Via the DCC/ERK1/2/NO/DCC Pathway

As disclosed herein, netrin-1 induces cardioprotection via the DCC/ERK1/2/NO/DCC pathway. Three netrin-1 receptors, DCC, neogenin and UNC5B, are present in the endothelial cells (ECs) of various vascular beds, and have been examined to date for their roles in angiogenic signaling. It was found that despite an absence of UNC5B, DCC and neogenin are abundantly expressed in C57BL/6J mouse heart, at both mRNA and protein levels. This was consistent with what was found earlier in adult ECs. Hearts perfused using a Langendorff system had an excessive myocardial infarction (MI, 42.5±3.6%) after global ischemia (20 min) and reperfusion (60 min), which was dramatically reduced by netrin-1 intervention (100 ng/ml, pre-perfusion 45 min, reperfusion 60 min) to 21.8±4.9%. This finding was accompanied by an augmented NO production. It was also demonstrated that this cardioprotective effect of netrin-1 was dependent on DCC, and consequent activations of ERK1/2 and eNOSs1177. Both cardiomyocytes and cardiac ECs were responsible for an increase in NO production, which feed-forwardly upregulated DCC expression. I/R-induced cardiac apoptosis was significantly attenuated by netrin-1. These results clearly demonstrate that netrin-1 protects heart tissue from I/R injury via a DCC/ERK1/2/eNOSs1177/NO/DCC feed-forward mechanism.

EXPERIMENTS

Materials: Purified mouse netrin-1 was purchased from R&D Systems (Minneapolis, Minn.). Polyclonal antibody for DCC was obtained from EMD Calbiochem (Gibbstown, N.J.). Polyclonal antibodies specific for phosphorylated ERK1/2, eNOSs1177 were obtained from Cell Signaling Technology (Danvers, Mass.). Polyclonal antibody specific for VEGFR2 was purchased from AbCAM (Cambridge, Mass.). Other chemicals were purchased from Sigma-Aldrich (St. Louis, Mo.) in the highest purity.

Animals: Male C57BL/6J mice (6-8 weeks old) were obtained from the Jackson Laboratories (Bar Harbor, Me.). DCC +/−mice were obtained from Dr. Marc Tessier-Lavigne from Genentech (South San Francisco, Calif.). Mice were housed under a pathogen-free condition. The use of animals and experimental procedures were approved by the Institutional Animal Care and Usage Committee at the University of California Los Angeles (UCLA).

RT-PCR and Western blot: Total RNA was extracted from mouse hearts using TRIzol (Invitrogen, Carlsbad, Calif.) according to the manufacturer's instructions. Reverse transcription was performed in standard fashion with iScript cDNA Synthesis Kit (Bio-Rad, Hercules, Calif.). PCR was performed using the following primer pairs:

```
                                            (SEQ ID NO: 1)
    DCC:       fw:      CAGCAAAAACTGTGCAAGGA
                                            (SEQ ID NO: 2)
               rev:     CGCAAAGTTCAGAATCGTCA;
```

-continued

| | | | |
|---|---|---|---|
| UNC5B: | fw: | AGTGTAATGGCGAGTGGGTC | (SEQ ID NO: 3) |
| | rev: | CGAAGAGTTCCTCCACTTGC; | (SEQ ID NO: 4) |
| Neogenin: | fw: | TGAACCAGTTGTGGGAAACA | (SEQ ID NO: 5) |
| | rev: | GCCACTCATTGGAGGTTTGT; | (SEQ ID NO: 6) |
| UNC5A: | fw: | CGTGTCCTGCACTTCAAAGA | (SEQ ID NO: 7) |
| | rev: | CCTGGTAGCTGACAAGGAGC; | (SEQ ID NO: 8) |
| UNC5C: | fw: | CACATCTGGAGTGGCTCTCA | (SEQ ID NO: 9) |
| | rev: | GCATAGCTTCTGCCGGATAG; | (SEQ ID NO: 10) |
| UNC5D: | fw: | GTAAAGCAGCTCAAGGTGGC | (SEQ ID NO: 11) |
| | rev: | ATGCAGCAGCTTTGGTTCTT; | (SEQ ID NO: 12) |
| α6: | fw: | GTGTGTGAACATCAGGTGCC | (SEQ ID NO: 13) |
| | rev: | ATATTCTGAGCAGCAGCGGT; | (SEQ ID NO: 14) |
| α3: | fw: | GCTGACCTGATCATCTGCAA | (SEQ ID NO: 15) |
| | rev: | GCAGTAGGACAGGAAGGCAG; | (SEQ ID NO: 16) |
| β4: | fw: | GAGAGCGAGAGGGTGTCATC | (SEQ ID NO: 17) |
| | rev: | ATATCTCCATTGGGCCTCCT. | (SEQ ID NO: 18) |

PCRs were carried out on an iCycler (Bio-Rad, Hercules, Calif.) including primers generated for GAPDH, ((95° C./2 min), (95° C./25 sec, 57° C./5 sec, 68° C. 5 min)×35, (72° C./10 min)). Western blot analysis was performed as previously published. See Youn et al. (2009) Circ. Res 104:50-59, which is herein incorporated by reference.

Langendorff perfusion: The mice were anesthetized with intraperitoneal pentobarbitone (60 mg/kg). Hearts were harvested and rapidly transferred into ice-cold Krebs-Henseleit buffer (KHB). The aorta was cannulated with a 20-gauge stainless steel blunt needle and transferred to the Langendorff rig and perfused retrograde instantly with modified Krebs-Henseleit buffer, which contained (in mmol/L): NaCl 118.0, KCl 4.7, $CaCl_2$ 2.5, $MgSO_4$ 1.2, $KH_2PO_4$ 1.2, $NaHCO_3$ 25.0, D-Glucose 10 at constant pressure (80±1 mmHg) using a peristaltic pump and feedback system.

Figure 7:
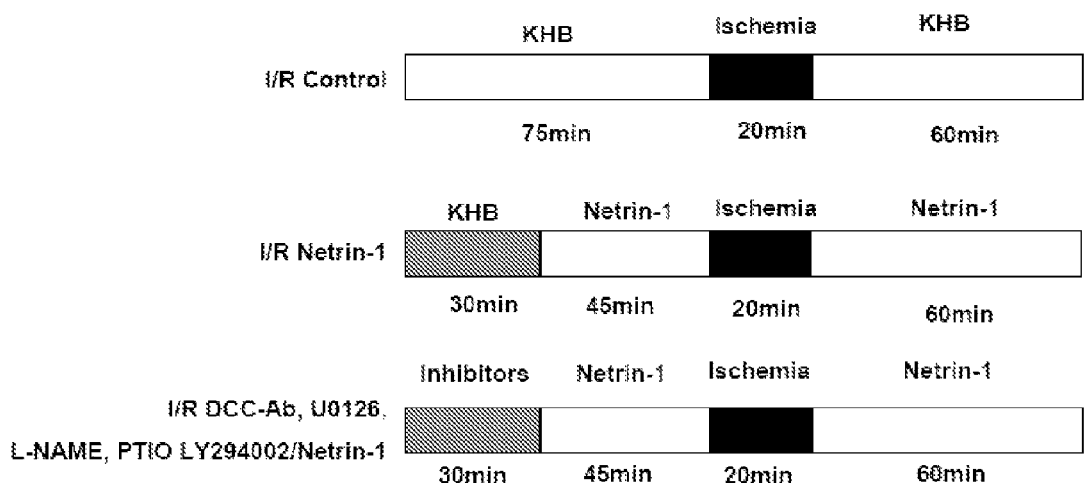
FIG. 7 is a diagrammatical description of experiment groups and the global ischemia/reperfusion protocol using a Langendorff perfused heart model.

For no I/R setting, hearts were perfused with KHB or netrin-1 for 120 min. For I/R setting, hearts were subjected to 30 min of perfusion with DCC-antibody (1 μg/ml), U0126 (50 μmol/L), L-NAME (100 μmol/L), PTIO (60 μmol/L) or KHB only, followed by 45 min netrin-1 (100 ng/ml) perfusion. Then I/R injury was consistently produced by subjecting the hearts to 20 min of normo-thermic ischemia, followed by reperfusion for 60 min with netrin-1. These experimental protocols are illustrated in FIG. 7.

Electron spin resonance detection of nitric oxide radical: Bioavailable nitric oxide radical (NO) from cells or tissues was detected using electron spin resonance (ESR) as described. See Nguyen et al. (2006) PNAS USA 103:6530-5; and Youn et al. (2009) Circ. Res 104:50-59, which are herein incorporated by reference. In brief, whole heart homogenates or cardiomyocytes were incubated with equal volume of freshly prepared NO-specific spin trap $Fe2+(DETC)_2$ colloid (0.5 mmol/L) for 60 min. Gently collected homogenates or cell suspensions were snap-frozen in liquid nitrogen and loaded into a finger Dewar for analysis with an eScan electron spin resonance (ESR) spectrophotometer (Bruker, Freemont, Calif.) at the following settings: center field, 3410; field sweep, 100 G; microwave frequency, 9.73 GHz; microwave power, 13.26 mW; modulation amplitude, 9.82 G; 512 points resolution and receiver gain, 356.

Infarct size analysis: Infarct size was determined by triphenyl tetrazolium chloride (TTC) staining In brief, at the end of the experimental protocol hearts were infused with 1% TTC in phosphate buffered solution (pH 7.4) for 10 min prior to snap freezing at −20° C. While frozen, the hearts were sliced perpendicular to the long-axis of the heart at 1 mm intervals and de-stained in 10% formaldehyde solution to increase contrast between necrotic and viable myocardium. The heart slices were then digitally photographed for planimetry using NIH Image 1.62. Infarct size is expressed as an infarct-to-risk zone ratio (the risk zone is the whole ventricular volume in this global ischemic model).

Creatine kinase (CK) release: The effluent was collected during the entire 60 min of reperfusion. The amount of CK was determined using a CK Reagent Set (Diagnostic Chemicals, Charlottetown, PE). CK reagent was reconstituted in 10 ml of buffer provided by the manufacturer. 40 μA of each sample was mixed with 1 ml of reconstituted reagent, incubated for 2 min at 37° C. and read at 340 nm by a Microplate Reader (BioTek, Winooski, Vt.). The results were normalized by protein concentration, which was determined by DC protein assay (Bio-Rad, Hercules, Calif.).

Spatial localization of NO: In order to visualize NO and to analyze its spatial localization in heart sections, the level of NO concentration was monitored using a fluorescent NO probe, DAF-FM Diacetate. Sections were loaded with DAF-FM Diacetate (10 μmol/L for 1 hr in DMSO), washed to remove excessive probe, and soaked in fresh buffer for an additional 30 min incubation to complete de-esterification of the intracellular diacetates. The sections were then mounted and visualized with a confocal microscope.

Isolation of adult mouse cardiomyocytes: The heart was retrogradely perfused (37° C.) at a constant pressure of 80 mm Hg for 5 min with a $Ca^{2+}$-free Tyrode buffer containing (in mmol/L): NaCl 130, KCl 5.4, $MgSO_4$ 1, $NaH_2PO_4$ 0.6, D-Glucose 10, HEPES 10, which was continuously bubbled with 95% $O_2$+5% $CO_2$. The enzymatic digestion was commenced by adding collagenase type II (Worthington Biochemical Corp., Lakewood, N.J., 0.56 mg/ml each) to the perfusion buffer and continued for 20 min. The heart was cut down and placed in the Petri dish with perfusion solution. The digested ventricular tissues were cut into 2-3 mm pieces and gently aspirated with a transfer pipette to facilitate cell dissociation. The myocytes were allowed to sediment by gravity for 8-10 min in the 15-ml Falcon tubes.

Detection of apoptosis: Apoptosis was detected by the apoptosis detection kit (Chemicon International, Inc., Billerica, Mass.) according to the manufacturer's protocol. At the end of the experimental protocols frozen heart sections (12 μm) were fixed with 1% formalin for 10 min at room temperature (RT) and washed twice in PBS, permeabilized with ethanol/acetic acid (2:1) for 5 min at −20° C., washed twice in PBS, and then incubated for >10 sec with the equilibration buffer. Subsequently, the sections were incubated for 1 hr with DIG-conjugated dUTP and TdT enzymes at 37° C., and then for 10 min in the stop buffer at room temperature (RT), and finally washed three times in PBS. The sections were then incubated with FITC-conjugated anti-DIG antibody for 30 min at RT, and washed three times in PBS.

Cover-slipped sections were mounted with medium containing 0.5 µg/ml of propidium iodide.

Statistical analysis: All data are presented as mean±SEM from four to six independent experiments (different individual mice or different passage of BAECs used on different days). NO data have been normalized by protein prior to statistical analysis. ANOVA was used to compare means of different experimental groups. Statistical significance is set as $p<0.05$.

Results

Netrin-1 stimulates NO production from mouse heart: RNA and protein samples were prepared from freshly isolated C57BL/6J mouse hearts. Quantitative reverse transcription polymerase chain reaction (qRT-PCR) and Western blot were used to determine mRNA and protein levels of netrin-1 receptors respectively. Relative abundance of each mRNA expression, indexed by endogenous GAPDH, was used for comparison. Whereas, DCC, UNC5A, integrin $\beta 1$ and $\alpha 3$ were abundantly expressed at mRNA levels, UNC5B, C, D and $\beta 4$ was undetectable (FIG. 1A). Neogenin and α6 were weakly expressed. It was also confirmed DCC and neogenin expression at protein level (data not shown). Perfusion of heart with netrin-1 (100 ng/ml, 120 min) resulted in a significant increase in NO production, as demonstrated by representative ESR spectra and grouped data from six independent experiments (FIG. 1B and FIG. 1C). Subsequent experiments indicate that netrin-1 also simulated DCC-dependent NO production from hearts exposed to I/R injury (see below).

Figure 2B:
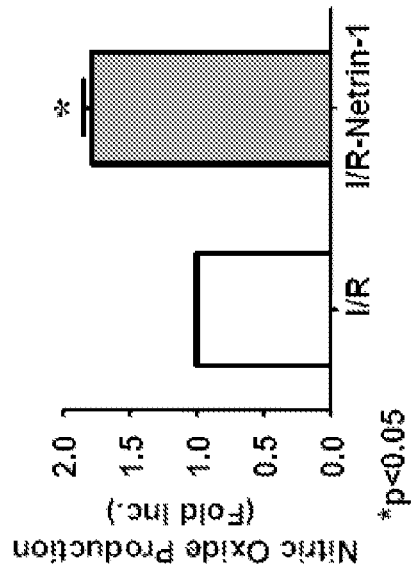
FIG. 2B is a graph which provides quantitative grouped data of infarct size (Means±SEM, n=5), *p<0.01.
Figure 2D:
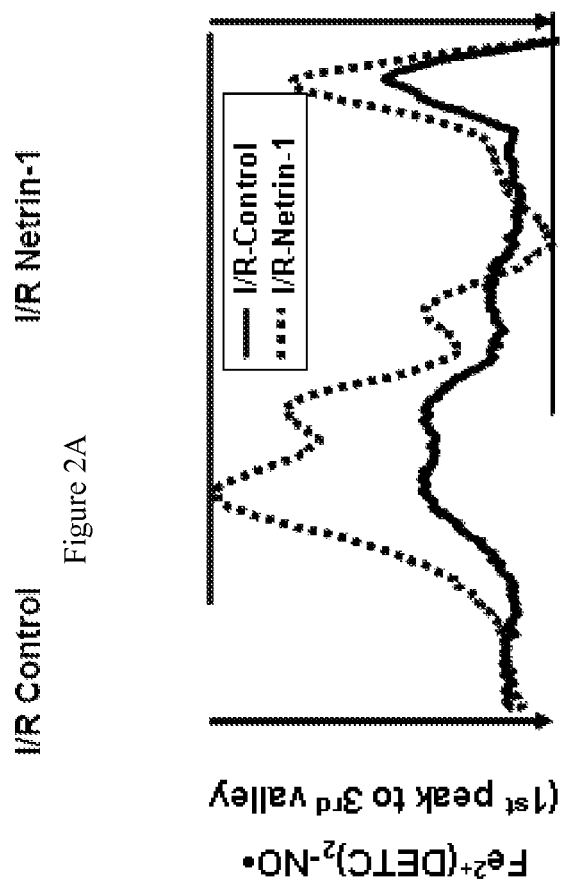
FIG. 2D provides grouped data of NO production from four independent experiments. *p<0.05.
Figure 2A:
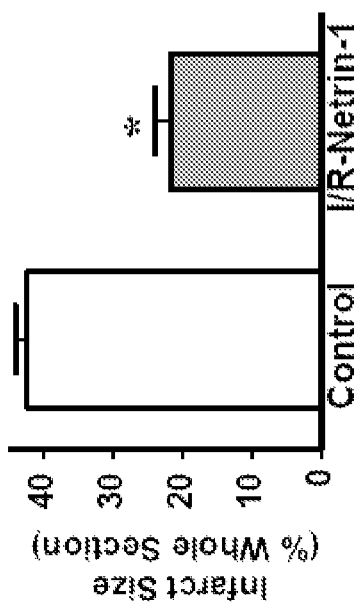
FIG. 2A shows pictures of heart sections which evidence that netrin-1 protects heart tissue from ischemia/reperfusion injury. Hearts were pre-perfused for 45 min with netrin-1 (100 ng/ml) before ischemia/reperfusion (20 min ischemia, 60 min reperfusion with netrin-1). Sections of hearts were stained with 2,3,5-TTC and infarct area calculated as % of risk area. Infarct size was significantly decreased in netrin-1 treated hearts from that of controls (21.8±4.9% vs. 42.5±3.6%, respectively, p<0.01). Color photographs of this figure are provided in Zhang & Cai (2010) J Molecular and Cellular Cardiology 48:1060-70, which is herein incorporated by reference.
Figure 2C:
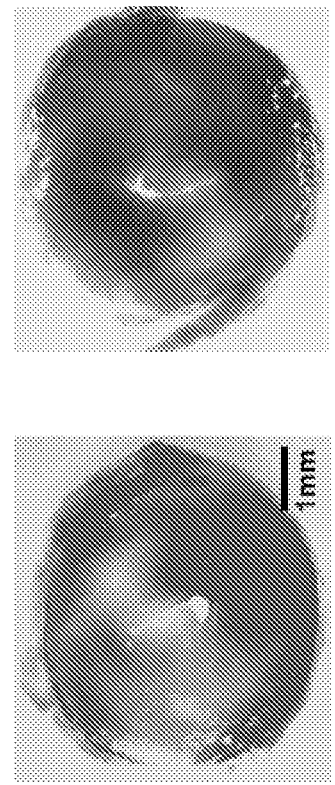
FIG. 2C shows representative ESR spectra (more than one spectrum) of NO production from hearts perfused with netrin-1.

Nitric oxide mediates netrin-1 induced cardiac protection from ischemia/reperfusion injury: In view of the potent effect of netrin-1 on cardiac NO production (FIG. 1B and FIG. 1C) and the potentially significant role of NO in mediating cardioprotection, whether netrin-1 induces cardioprotection during I/R injury was examined. Hearts pre-perfused for 45 min with netrin-1 (100 ng/ml) were subjected to 20 min global ischemia, followed by a 60 min reperfusion with netrin-1. The experimental protocol is illustrated in FIG. 7. Infarct size was quantitated as the area not stained red with tetrazolium red. Netrin-1 treated hearts had a substantial reduction in infarct size compared to untreated controls (21.8±4.9% vs. 42.5±3.6% for netrin-1 treated I/R vs. I/R alone, $p<0.01$) (FIG. 2A and FIG. 2B). This was accompanied by an augmented production of NO in netrin-1 treated, I/R-ed hearts (1.78±0.12 fold higher than the untreated I/R controls, FIG. 2C and FIG. 2D).

Figure 3B:
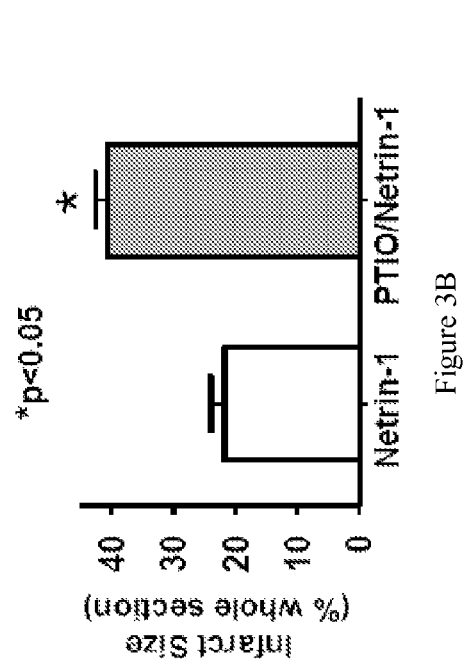
FIG. 3B is a graph which provides quantitative grouped data of infarct size (Means±SEM, n=5), *p<0.05.
Figure 3D:
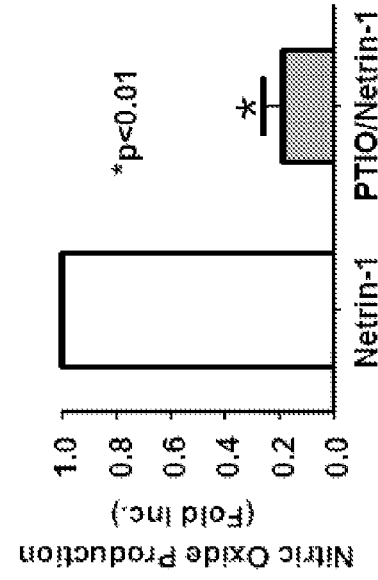
FIG. 3D provides grouped data of NO production from three independent experiments, *p<0.001.
Figure 3A:
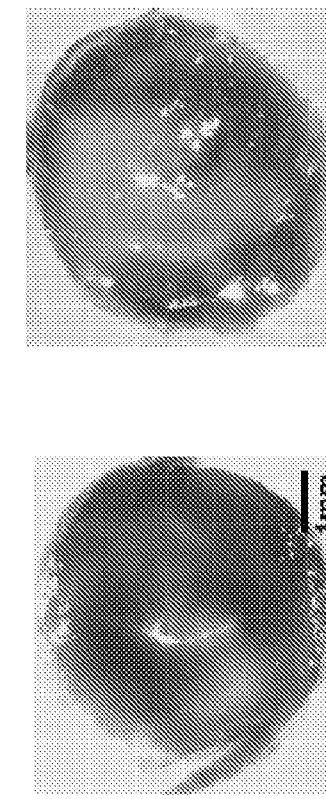
FIG. 3A provides pictures of sections of hearts showing that nitric oxide is required for netrin-1 induced cardiac protection from ischemia/reperfusion injury. Hearts were pre-perfused with PTIO for 30 min prior to netrin-1 perfusion (100 ng/ml, 45 min), followed by ischemia/reperfusion (20 min ischemia, 60 min reperfusion with netrin-1). Sections of hearts were stained with 2,3,5-TTC and infarct area calculated as % of risk area. Color photographs of this figure are provided in Zhang & Cai (2010) J Molecular and Cellular Cardiology 48:1060-70, which is herein incorporated by reference.
Figure 3C:
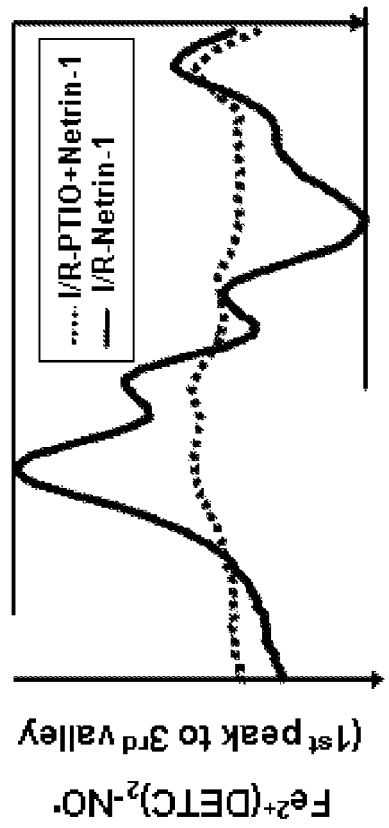
FIG. 3C shows representative ESR spectra of NO production from hearts perfused with netrin-1.

To determine whether the cardioprotective effect of netrin-1 was dependent on NO, mouse hearts were subjected to NO scavenger PTIO (60 µmol/L, 30 min) prior to netrin-1 perfusion and I/R injury. While NO production was attenuated (FIG. 3C and FIG. 3D), the infarct size in PTIO-pretreated, netrin-1-perfused hearts was also reversed to near control levels of 40.6±4.2% (FIG. 3A and FIG. 3B), implicating that the cardioprotective effects of netrin-1 is indeed, NO-dependent.

Figure 4A:
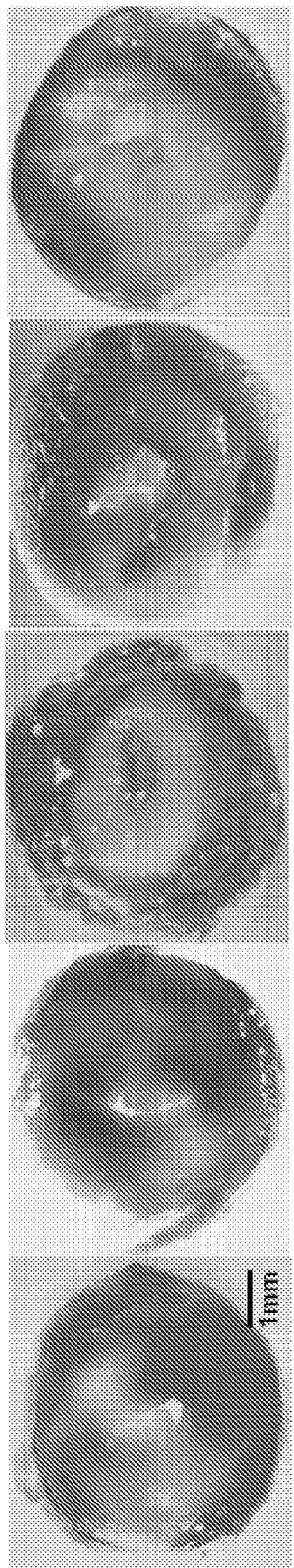
FIG. 4A shows sections of hearts that evidence that DCC/ERK1/2 activation is required for netrin-1-induced cardioprotection. Hearts were perfused with DCC antibody (1 µg/ml), ERK1/2 inhibitor U0126 (1,4-diamino-2,3-dicyano-1,4-bis (2-aminophenylthio)butadiene, 50 µmol/L) or L-NAME (nitro-L-arginine methyl ester, 100 µmol/L) for 30 min prior to 45 min netrin-1 perfusion. Ischemia/reperfusion injury was consistently produced by subjecting the hearts to 20 min of ischemia, followed by reperfusion for 60 min (with or without netrin-1). Sections of hearts were stained with 2,3,5-TTC and infarct area calculated as % of risk area. Representative TTC stains of control hearts, and hearts receiving netrin-1, DCC-antibody/netrin-1, U0126/netrin-1 and L-NAME/netrin-1. Color photographs of this figure are provided in Zhang & Cai (2010) J Molecular and Cellular Cardiology 48:1060-70, which is herein incorporated by reference.
Figure 4C:
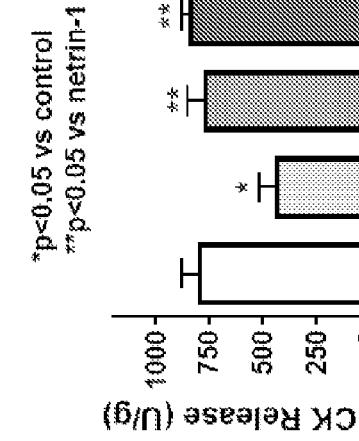
FIG. 4C is a graph showing creatine kinase (CK) release which was measured by collecting effluent during the entire 60 min of reperfusion from control hearts, and hearts receiving netrin-1, DCC-antibody/netrin-1, U0126/netrin-1 and L-NAME/netrin-1 (Means±SEM, n=3). *p<0.05 vs. control; **p<0.05 vs netrin-1.
Figure 4B:
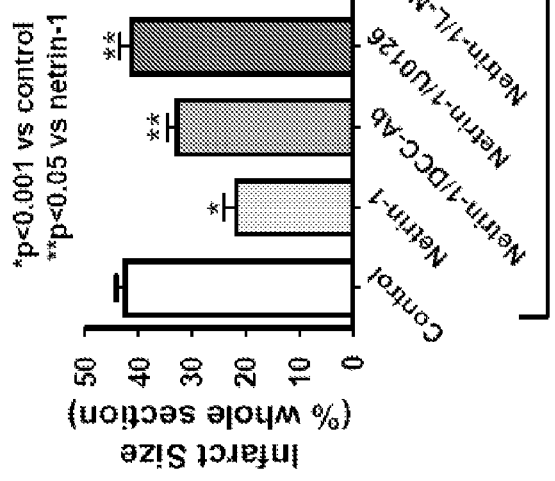
FIG. 4B graphically provides the infarct size shown in quantitative grouped data of FIG. 4A (Means±SEM, n=5), *p<0.001 vs. control; **p<0.05 vs netrin-1.
Figure 4E:
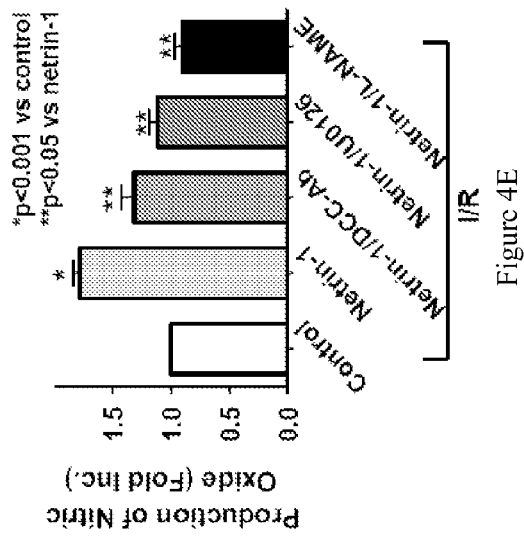
FIG. 4E is a graph of the grouped data of NO production of FIG. 4D (Means±SEM, n=5). *p<0.001 vs. control, **p<0.05 vs. netrin-1.
Figure 4G:
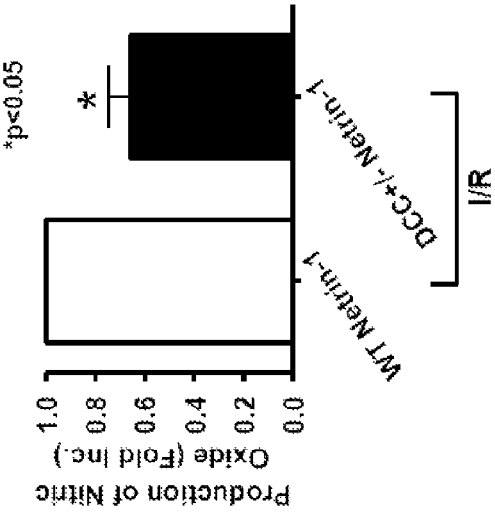
FIG. 4G provides grouped data of NO production of FIG. 4F (Means±SEM, *p<0.05).
Figure 4D:
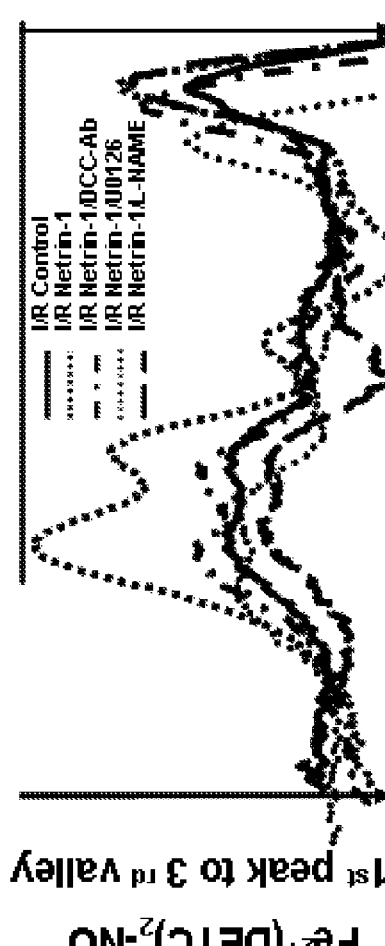
FIG. 4D shows representative ESR spectra of NO production of control hearts, and hearts receiving netrin-1, DCC-antibody/netrin-1, U0126/netrin-1 and L-NAME/netrin-1.

DCC/ERK1/2 is required for netrin-1 induced cardioprotection: DCC-dependent activation of the mitogen activated protein kinase ERK1/2 has been found a signal transduction pathway for netrin-1 stimulated NO production in vascular ECs. Next, whether a similar signaling cascade is the mechanism whereby netrin-1 increases NO production in the heart was examined. Hearts were pre-perfused with antibody neutralizing DCC, MEK1/2 inhibitor U0126 or NOS inhibitor L-NAME for 30 min prior to netrin-1 perfusion. The apparent cardioprotective effects of netrin-1 were reversed (n=4 for all): the infarct size was increased upon addition of DCC antibody (32.7±4.5%), U0126 (41.3±4.1%) or L-NAME (40.9±7.2%), compared to netrin-1 treatment alone (21.8±4.9%) (FIG. 4A and FIG. 4B). In addition, creatine kinase (CK) release, as an index of cardiac muscle damage, showed identical responses (FIG. 4C). Concomitantly, increased NO production by netrin-1 (1.78±0.12 fold vs. untreated I/R controls) was also attenuated by DCC antibody (1.31±0.21 fold vs. untreated I/R controls), U0126 (1.12±0.15 fold vs. untreated I/R controls) or L-NAME (0.90±0.13 fold vs. untreated I/R controls) (FIG. 4D and FIG. 4E). These results indicate that NO-dependent cardioprotective effect of netrin-1 is mediated by DCC-dependent activation of ERK1/2 and eNOS.

Figure 4F:
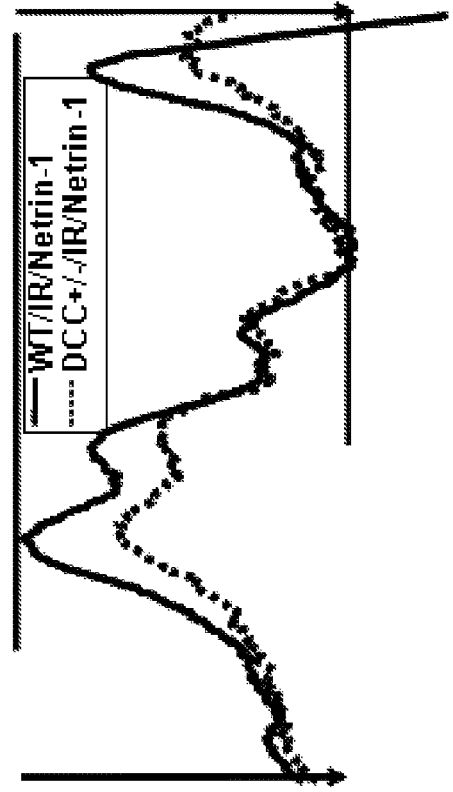
FIG. 4F provides representative ESR spectra of NO production from IR-ed hearts of WT or DCC +/−mice perfused with netrin-1.

In additional experiments, hearts from wild type (WT) and DCC +/−mice were subjected to I/R and netrin-1 perfusion. Netrin-1 provoked NO production in I/R-ed DCC +/−hearts was significantly reduced (0.66 fold ±0.15, $p<0.05$, FIG. 4F and FIG. 4G) comparing to age-matched WT hearts. Netrin-1 induced reduction in infarct size in WT hearts was also markedly attenuated (infarct size: 21.8±4.9% vs. 35.9±3.2% for WT vs. DCC +/−respectively, $p<0.05$, FIG. 4H and FIG. 4I). These data further implicate an intermediate role of DCC in mediating netrin-1 induced cardioprotection.

Figure 5C:
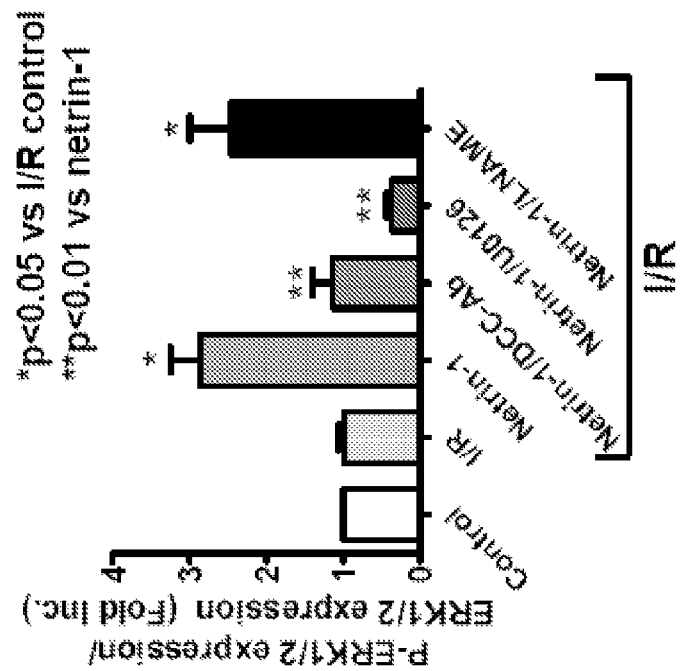
FIG. 5C shows grouped densitometric data of ERK1/2 phosphorylation that is normalized by ERK1/2 (n=3), *p<0.05 vs I/R control, **p<0.01 vs netrin-1.
Figure 5B:
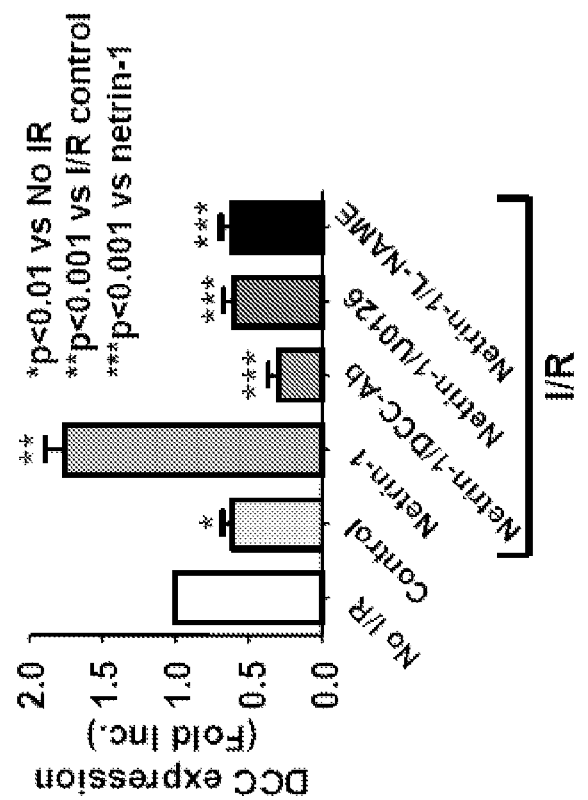
FIG. 5B shows grouped densitometric data of DCC protein expression (n=6), *p<0.01 vs no I/R; p<0.001 vs I/R control. *p<0.001 vs netrin-1.
Figure 5E:
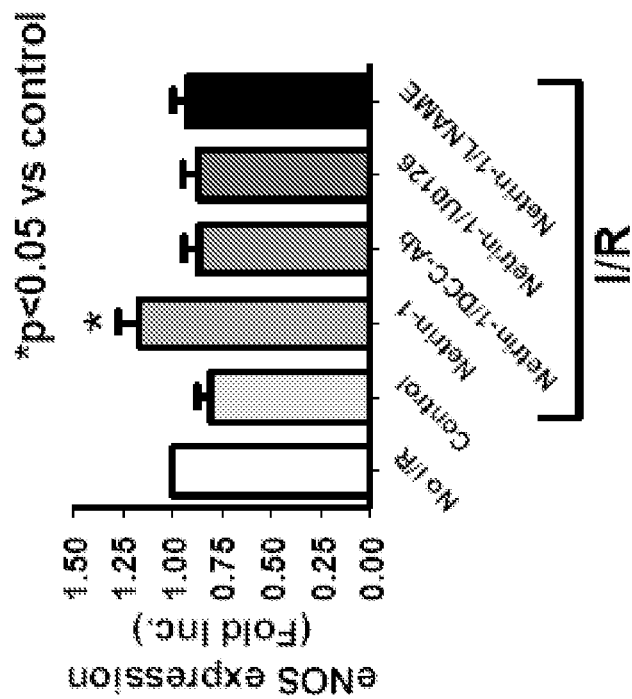
FIG. 5E shows grouped densitometric data of eNOS protein expression (n=5), *p<0.05 vs I/R control.
Figure 5D:
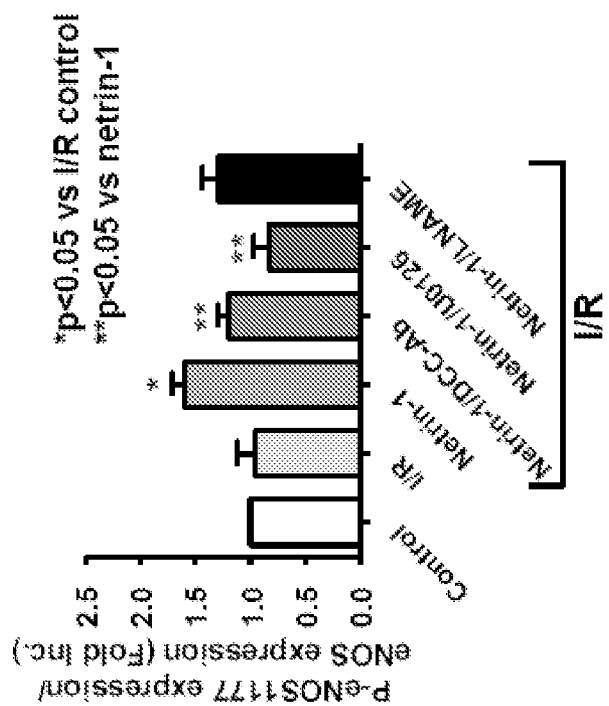
FIG. 5D shows grouped densitometric data of eNOS$_{s1177}$ phosphorylation that is normalized by eNOS (n=4), *p<0.01 vs I/R control, **p<0.01 vs netrin-1.
Figure 5G:
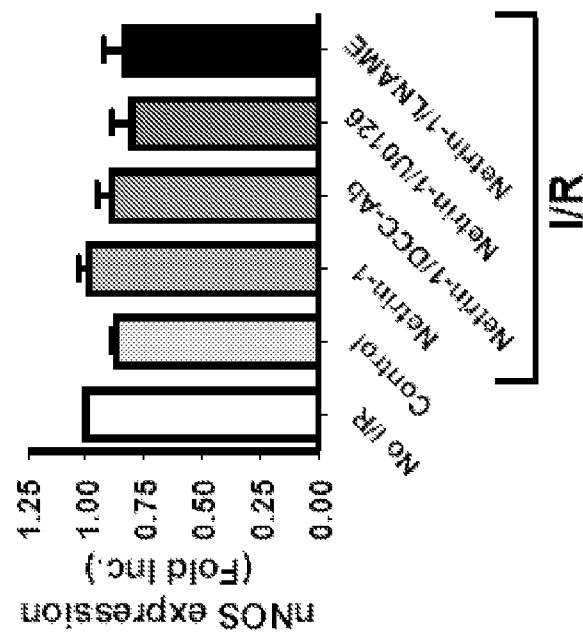
FIG. 5G shows grouped densitometric data of nNOS protein expression (n=3).
Figure 5F:
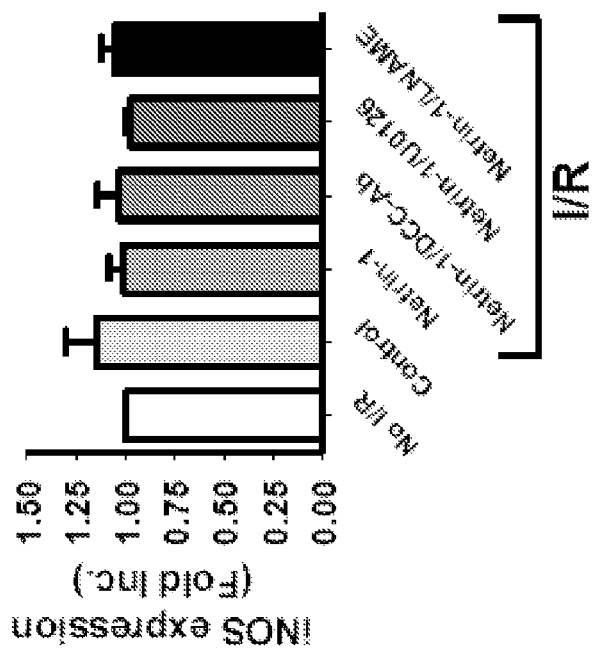
FIG. 5F shows grouped densitometric data of iNOS protein expression (n=4).
Figures 5H, 5I:
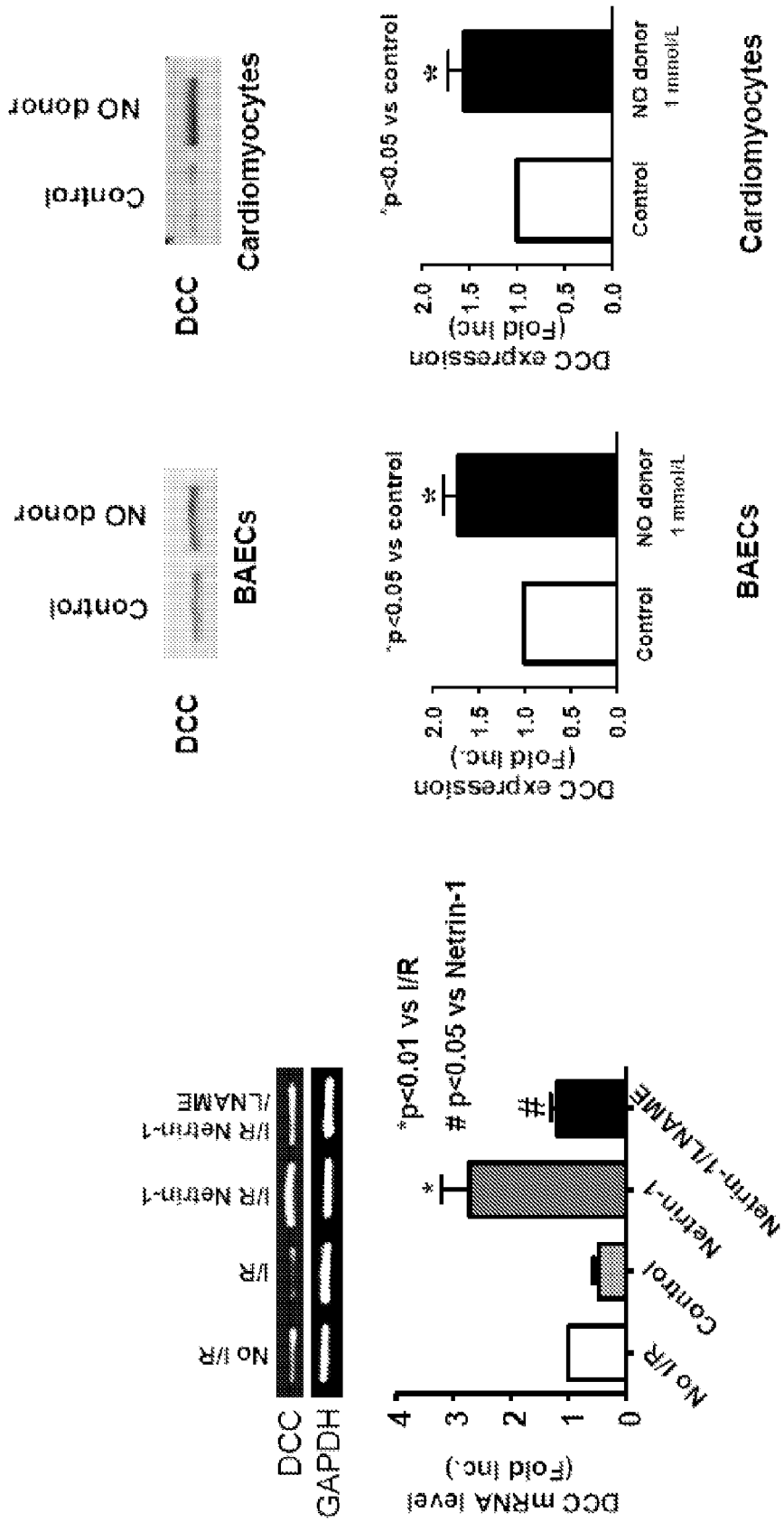
FIG. 5H shows a representative Western blot and grouped mRNA levels of RT-PCR analysis of DCC in post netrin-1-perfused hearts (n=3), *p<0.05.
FIG. 5I shows representative and grouped Western blot data of DCC expression in NO donor-treated BAECs and cardiomyocytes.
Figure 5J:
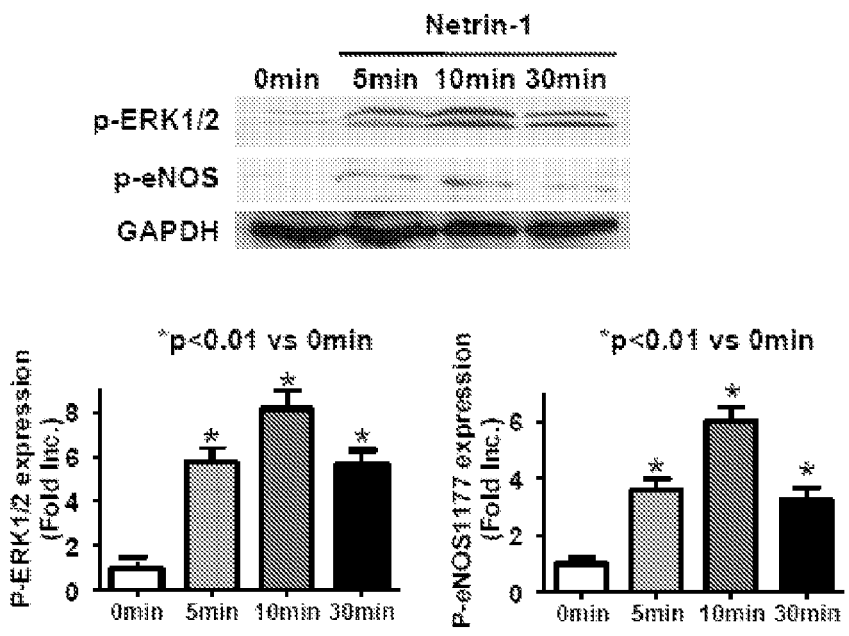
FIG. 5J shows representative and grouped Western blots data of ERK1/2 and eNOS$_{s1177}$ phosphorylation at different time points. Hearts were perfused with netrin-1 (100 ng/ml) and harvested at 0, 5, 10 and 30 min for Western blot analysis.

Furthermore, DCC protein abundance, ERK1/2 phosphorylation and eNOSs1179 phosphorylation were all increased, as evidenced by representative Western blots and quantitative data (FIGS. 5A-D). Interestingly, I/R alone induced a rapid decline in DCC protein and mRNA expression (FIG. 5B and FIG. 5H). Netrin-1 perfusion of I/R hearts led to a significant restoration of DCC protein expression, which was abolished by DCC-antibody, U0126, or L-NAME (FIG. 5B), indicating a potential feed-forward loop of NO-ERK1/2-DCC. Bovine aortic endothelial cells (BAEC) and isolated cardiomyocytes were treated with NO donor MAMANOATE (1 mmol/L, 2 hr) prior to analysis of DCC expression. Of note, NO donor increased DCC protein expression in both cultured ECs and cardiomyocytes (FIG. 5I). In additional experiments, hearts were perfused with netrin-1 and harvested at 0, 5, 10 and 30 min. Netrin-1 stimulation resulted in a rapid, time-dependent increase in ERK1/2 and eNOSs1177 phosphorylations (for 0, 5 and 10 min time points), which lasted up to 30 min (longest time point examined, FIG. 5J). Of note, RNA samples extracted from netrin-1-perfused I/R hearts demonstrated an elevation in DCC mRNA levels (FIG. 5H) as well, indicating that transcriptional regulation may have occurred to contribute to protein changes.

Moreover, a clear increase in phosphorylated ERK1/2 (FIG. 5C) and eNOSs1177 (FIG. 5D) was observed with netrin-1 treatment (n=6), which was inhibited by DCC-antibody or U0126, but not by addition of L-NAME. These results seem to indicate that netrin-1 initiates its signaling by binding to DCC, resulting in ERK1/2/eNOS activation to produce NO, which in turn, upregulates DCC to form a positive feedback loop. Furthermore, protein expression of eNOS was upregulated by netrin-1 perfusion under I/R condition, whereas iNOS and nNOS expression were unaffected (FIGS. 5A, E-G).

Figure 8:
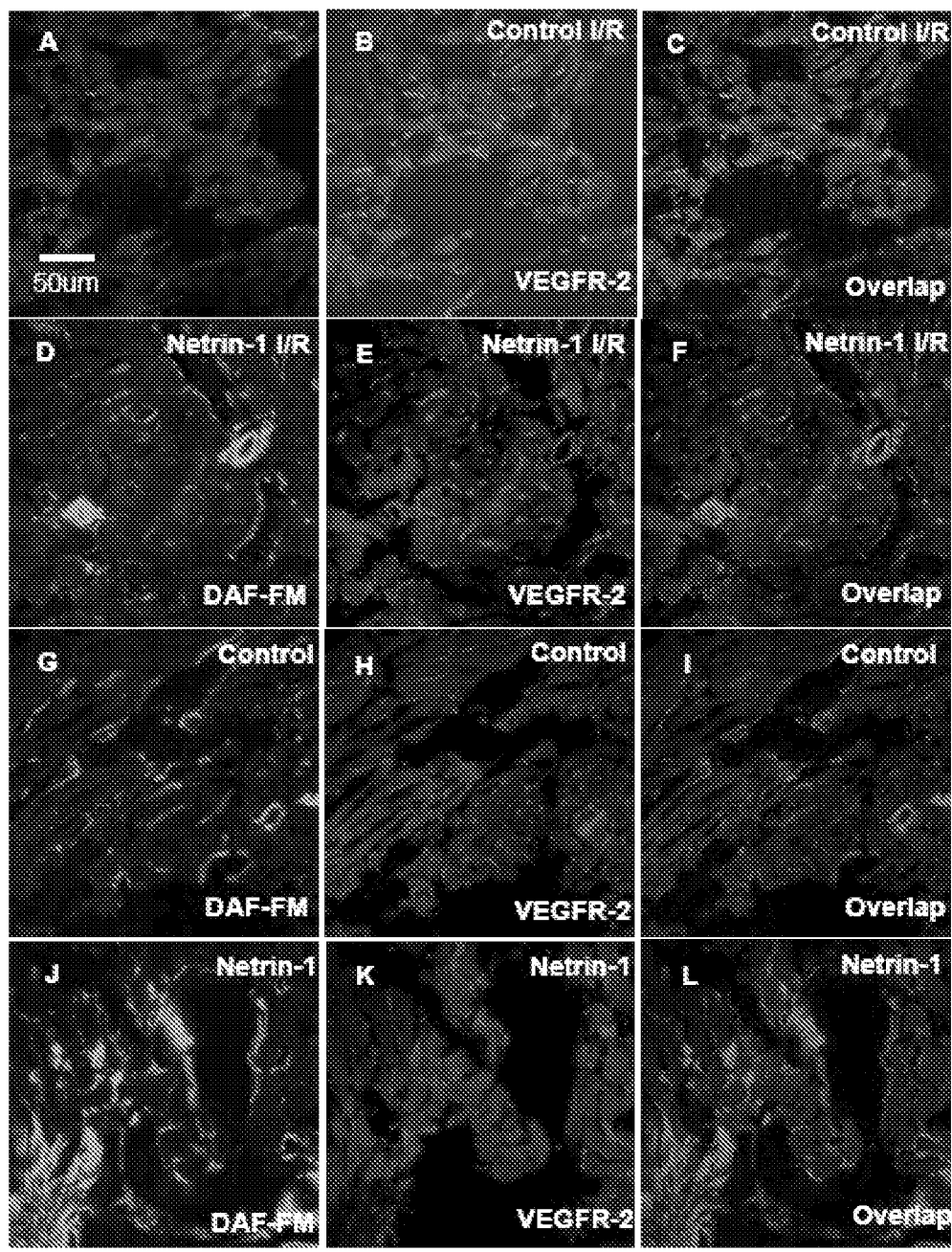
FIG. 8 shows micrographs of heart sections showing that netrin-1 stimulates NO production from both cardiac endothelial cells and myocytes. Hearts were perfused with netrin-1 with or without ischemia/reperfusion (I/R). Sections of the hearts were incubated with DAF-FM diacetate (first column) and anti-VEGFR2 antibody (second column). The third column is an overlap of the first column and the second column micrographs. Representative micrographs are presented for the following groups (panels A-C) I/R control; (panels D-F) I/R netrin-1; (panels G-I) Control without I/R; (panels J-L) Netrin-1 without I/R.
Figure 9E:
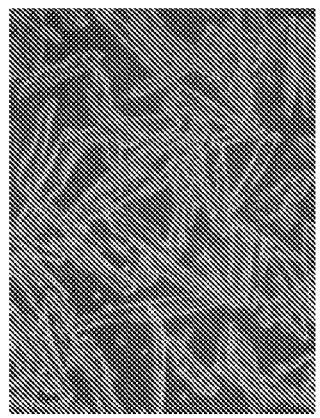
Figure 9F:
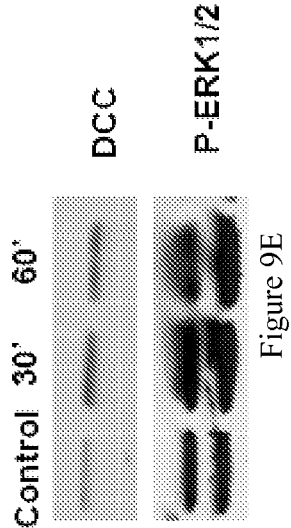
Figure 10:
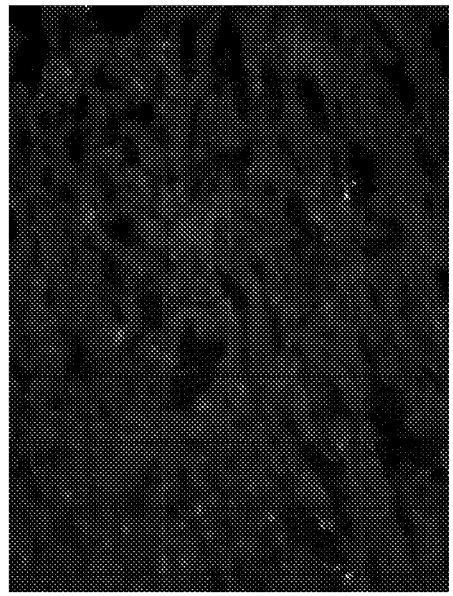
FIG. 10 evidences that netrin-1 perfusion enhances accumulation/production of netrin-1 in the mouse heart. Wild type mouse hearts were perfused with Krebs-Henseleit buffer (KHB) or KHB containing netrin-1 as indicated in FIG. 7, and sections were stained with netrin-1 antibody (light gray to white=green). Representative micrographs are presented.

Cardiomyocytes and ECs-derived NO production in response to netrin-1: The NO-specific fluorescent probe DAF-AM was used to estimate changes in NO production in left ventricle. In netrin-1 perfused, post-I/R heart NO staining was clearly increased (FIG. 8, panels A, D, G, J). As shown in FIG. 8, panels C, F, I, L, some of the increase in NO staining was detected specifically in the ECs that line cardiac, which also labeled positive for VEGFR2 fluorescent antibody (FIG. 8, panels B, E, H, K). The rest of the NO staining seemed to come primarily from cardiomyocytes, and showed an increase in netrin-1 treated myocardium.

To further investigate a specific role of cardiomyocytes in netrin-1 signaling in the heart, cardiomyocytes were freshly isolated from hearts and treated with netrin-1 (30 min or 60 min) in Tyrode's solution. There was a significant increase in NO production from cardiomyocytes treated with netrin-1, as demonstrated by representative ESR spectra and grouped data from three independent experiments (FIGS. 9A-D). Protein abundance of DCC and ERK1/2 phosphorylation were also significantly elevated in netrin-1-treated cardiomyocytes (FIG. 9E), echoing results found in lysed cardiac tissues (FIG. 5B). These results seem to suggest that netrin-1-stimulated NO production from cardiomyocytes is also DCC-dependent, and requires activation of ERK1/2 and eNOS.

Figure 6A:
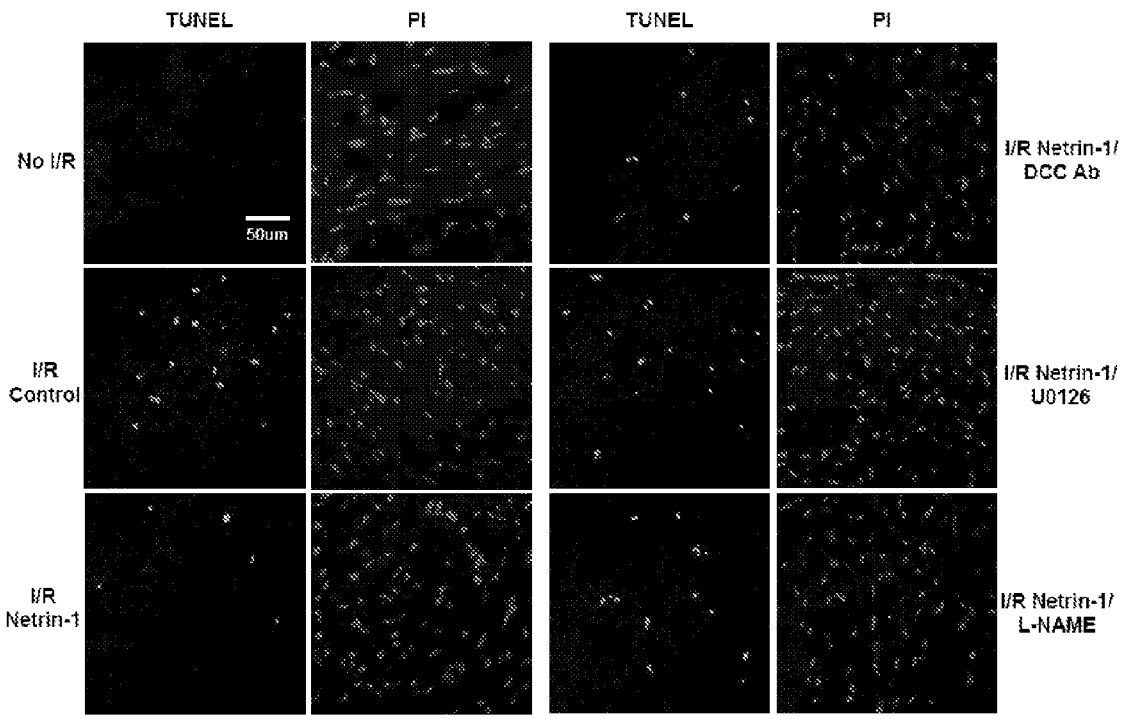
FIG. 6A shows that netrin-1 reduces cardiomyocyte apoptosis in post-I/R hearts: Hearts perfused as described in FIG. 4A. Representative detection of I/R-induced apoptotic cells by TUNEL, and of all the cells by Propidium Iodide (PI), in heart sections of the following conditions: control, ischemia/reperfusion (I/R), netrin-1 treated I/R, netrin-1/DCC I/R, netrin-1/U0126 I/R or Netrin-1/L-NAME I/R. Color photographs of this figure are provided in Zhang & Cai (2010) J Molecular and Cellular Cardiology 48:1060-70, which is herein incorporated by reference.
Figure 6B:
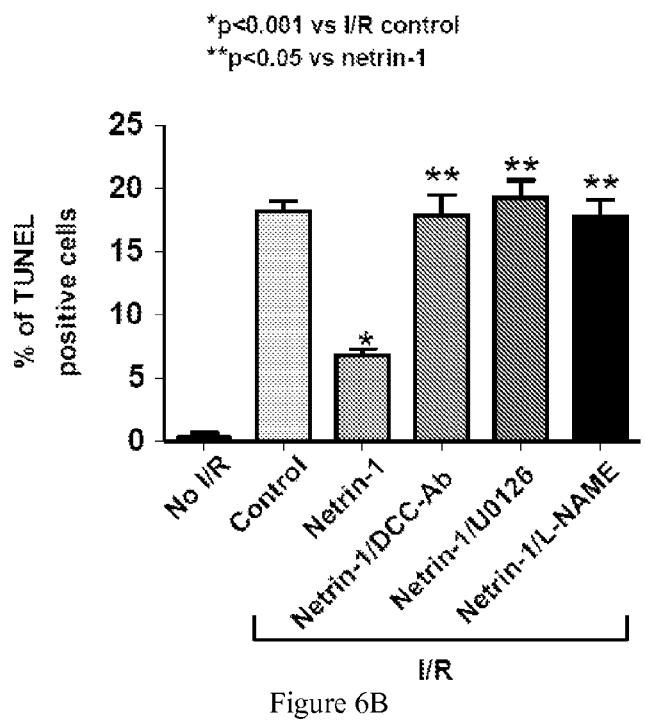
FIG. 6B shows grouped data from three independent experiments. *p<0.001 vs I/R control, **p<0.05 vs netrin-1.

Netrin-1 protects cardiac cells from apoptosis: NO protects ECs and cardiomyocytes from apoptosis induced by oxidant stress, inflammatory cytokines and chemotherapeutic agents. See Walford et al. (2003) J Thromb Haemost 1:2112-8; Chang et al. (1996) Am J Physiol 270:L931-40; Monastyrskaya et al. (2002) Nitric Oxide 7:127-31; and Hida et al. (2004) J Lab Clin Med 144:148-55. TUNEL assay was performed to determine whether netrin-1 inhibits apoptotic cell death induced by I/R. Left ventricular sections were incubated with FITC-conjugated anti-DIG antibody and coverslipped with the mounting medium containing 0.5 µg/ml of Propidium Iodide (PI). Representative TUNEL ($1^{st}$ and $3^{rd}$ columns, gray to white=green) and PI ($2^{nd}$ and $4^{th}$ columns, gray to white=red) stained sections and quantitative analysis are shown in FIG. 6A and FIG. 6B. I/R injury led to a significant increase in the percentage of TUNEL-positive cells compared to the non-I/R sections (18.2±1.45% vs. 0.33±0.5%). The heart pre-treated with netrin-1 exhibited a significant decrease in TUNEL positive cells (6.78±0.93%). The decrease in apoptosis was completely attenuated by DCC-antibody (17.83±2.87%), U0126 (19.24±2.4%) or L-NAME (17.82±2.19%), again consistently indicating intermediate roles of DCC, ERK1/2 and NO.

Discussion

The most significant finding herein is the identification of a DCC/ERK1/2/eNOSs 1177/NO/DCC/NO pathway that protects the heart from I/R induced apoptotic cell death and infarction. NO is produced following a DCC-dependent ERK1/2-eNOSs1177 activation in both cardiomyocytes and cardiac ECs, and that elevation in DCC expression was abolished by inhibition of ERK1/2 or NO, revealing a feed-forward loop of DCC-ERK1/2-NO-DCC. I/R induced a rapid loss in DCC protein and mRNA expression, which was recovered by netrin-1 to a level that was two fold of the control. Exogenous NO donor also upregulated DCC expression in both cultured myocytes and cardiac ECs.

Despite having been well characterized for its role in regulating axonal guidance, any potential effects of circulating netrin-1 on the pathophysiology of the cardiovascular system remain largely elusive. While recent studies identified an angiogenic role of netrin-1, whether it affects cardiac function is completely unknown. Thus, as provided herein, the effects of netrin-1 perfusion on cardiac protection and the expressional profiles in the heart of eight known netrin-1 receptors were examined. As demonstrated in FIG. 1, DCC, neogenin, UNC5A, integerin β1 and α3 were found highly expressed in C57BL/6J mouse hearts (mRNA detected by RT-PCR). Among these DCC and neogenin are attractive receptors that mediate axonal outgrowth, and both expressed in cultured endothelial cells; however, only DCC mediates netrin-1 stimulated NO production and endothelial cell growth and migration. The repulsive receptor UNC5B however was not expressed in mouse heart (FIG. 1), although found in endothelial cells previously. The mouse hearts used for these analysis were rinsed out of blood completely using Krebs-Henseleit buffer, so that the mRNA extracted was not contaminated by those of blood cells. If using uncleaned hearts or monocytes, abundant UNC5B mRNA was detected (data not shown), which is consistent to previous findings that monocytes express large amount of UNC5B. See Ly et al. (2005) PNAS USA 102:14729-34, which is herein incorporated by reference.

The concept that NO is a powerful cardioprotectant against I/R injury has become well accepted. See Jones & Bolli (2006) J Mol Cell Cardiol 40:16-23. Whereas in eNOS deficient mice the infarct size is significantly augmented following I/R injury, overexpression of eNOS is associated with reduced infarct size. See Jones et al. (1999) Am J Physiol 276:H1567-73; and Brunner et al. (2003) Cardiovasc Res 57:55-62. Nitrite supplementation results in a 48% reduction in infarct size post I/R insult. See Duranski et al. (2005) J Clin Invest 115:1232-40; Bryan et al. PNAS USA (2007) 104: 19144-9; Hendgen-Cotta et al. (2008) PNAS USA 105:10256-61; and Moens et al. (2008) Circulation 117:1810-9. Indeed, NO has been shown to mediate cardioprotective effects of estrogen, statins, moderate alcohol, peroxisome proliferator-activated receptor-alpha and sildenafil. See Fraser et al. (2000) Cardiovasc Res 46:111-8; Di Napoli et al. (2001) Cardiovasc Res 51:283-93; Abou-Agag et al. (2005) Free Radic Biol Med 39:540-8; Bulhak et al. (2006) Basic Res Cardiol 101:244-52; and Elrod (2007) Am J Physiol Heart Circ Physiol 292:H342-7. As shown herein, netrin-1 induced an approximate 2-fold increase in cardiac NO production, which was associated with a 49% decrease in infarct size following I/R injury. The specific, NO-mediated cardioprotective effect of netrin-1 was abolished by NO scavenger PTIO (FIG. 3) and NOS inhibitor L-NAME (FIG. 4). Thus; this data further establishes a cardioprotective role of NO and reveals the mechanisms whereby netrin-1 exhibits cardioprotection.

These findings support an essential role of DCC in mediating netrin-1 induction of NO in cardiac ECs and myocytes. DCC-antibody abolishes netrin-1 induction of NO production in I/R-ed hearts. DCC protein abundance and mRNA expression were increased in netrin-1-perfused, I/R-ed hearts, although I/R alone induced a decline in DCC protein and mRNA expression (FIGS. 5A, 5B, 5I). NO donor also upregulated DCC protein expression in both cultured ECs and cardiomyocytes (FIG. 5H). These data reveal a feed-forward loop of DCC-NO-DCC, and a predominant role of DCC in mediating netrin-1-dependent cardioprotection. Though the expression of neogenin was abundant, neogenin-antibody had no effect on netrin-1 stimulated NO production or cardioprotection (data not shown).

Netrin-1 perfusion resulted in marked increases in ERK1/2 (FIG. 5C) and eNOSs1177 (FIG. 5D) phosphorylations, which were inhibited by DCC-antibody or U0126, but not by addition of L-NAME. These seem to suggest that netrin-1/DCC/ERK1/2/eNOS pathway is turned on first, as inhibition of NO production was ineffective in preventing DCC/ERK activation, whereas, the secondary feed-forward mechanism of NO/DCC/ERK1/2 occurs later, as DCC-antibody and U0126 blocked eNOS phosphorylation. The role of ERK1/2 in mediating netrin-1 activation of eNOS is similar to previous observations that ERK1/2 is involved in transient activation of eNOS by ROS. See Cai et al. (2003) Mol Pharmacol 63:325-31; and Chen et al. (2004) Endocrinology 145:113-25. It is interesting to speculate that this may share similarities with ROS-dependent preconditioning. Recent studies by Das et al demonstrated that ERK1/2 phosphorylation mediates sildenafil-induced myocardial protection against I/R injury in mice. See Das et al. (2009) Am J Physiol Heart Circ Physiol 296:H1236-43. Previous studies also demonstrated that ERK1/2 mediates NO donor stimulated apoptotic reduction during I/R. See Li et al. (2006) Apoptosis 11:923-30. Transgenic mice with activated MEK1/ERK2 have protected myocardium when exposed to I/R insult in vivo. See Lips et al. (2004) Circulation 109:1938-41. Confirming a cardioprotective role of ERK1/2, this data also evidences a netrin-1/DCC/ERK1/2/eNOS/NO/DCC feed-forward loop that mediates the cardioprotective effects of netrin-1.

The role of the PI3K/AKT pathway in mediating netrin-1 induced cardioprotection was also studied. Following the same I/R protocol outlined in FIG. 7, it was found that after the entire I/R procedure, AKT phosphorylation was minimal and unaffected by DCC-Ab, U0126 or L-NAME (data not shown), although this data does not rule out the possibility that AKT was more active at earlier time points. LY294002 pretreatment also failed to reduced netrin-1 stimulated NO production (data not shown), implicating that PI3K/AKT pathway is not required for netrin-1 stimulation of NO production in this particular Langendorff perfusion model.

Netrin-1 induced reduction in myocardial injury, is at least in part, mediated by NO-dependent decrease in myocardial apoptosis. TUNEL-positive cardiomyocytes were decreased by 62.7% in netrin-1 treated hearts than that of controls. Apoptosis has been observed previously in hearts subjected to either continuous ischemia or ischemia followed by reperfusion. See Gottlieb et al. (1994) J Clin Invest 94:1621-8; and Buerke et al. (1995) PNAS USA 92:8031-5. One of the major protective mechanisms of NO has been shown to be prevention of myocardial apoptosis/death. See Liu et al. (2007) J Am Coll Cardiol 50:808-17. Indeed, myocardial apoptosis was significantly increased in eNOS-deficient mice during fetal and neonatal heart development, implicating that basal NO release from eNOS protects cardiomyocytes from apoptosis. See Feng et al. (2002) Circulation 106:873-9. Weiland et al. have also shown that inhibition of endogenous eNOS potentiates I/R induced myocardial apoptosis via caspase 3 pathway. See Weiland et al. (2000) Cardiovasc Res 45:671-8. Consistent to these observations, this data demonstrated that inhibition of netrin-1 signaling to attenuate NO production resulted in loss of the cardioprotective effects of netrin-1.

In summary, netrin-1 exerts its powerful cardioprotective effect during I/R injury. Upon netrin-1 perfusion, its attractive receptor DCC is activated, resulting in ERK1/2/eNOS$s_{1177}$ activation, which in turn, produces NO to upregulate DCC expression, forming a feed-forward loop to maintain DCC activity and additional NO production. A persistent supply of NO may thus underlie the marked reductions in infarct size and cardiac apoptosis. It is very important to note that the cardioprotective treatment effects of netrin-1 are uniquely different from NO donors: 1) Netrin-1 is a physiologically produced protein that is less likely to exert adverse effects, because it produces the optimal amount of NO that is protective. It is well known that too much NO is cytotoxic and damaging. One of the drawbacks of using NO donors for treatment is the difficulty to ensure the right amount of NO is released and maintained at the target tissue. 2) As shown by data in the sections 2 and 4 below, in addition to producing NO, netrin-1 potently reduces superoxide production via attenuation of NOX4 upregulation and mitochondrial damage. It also inhibits endothelial progenitor cell apoptosis and neointimal formation, therefore beneficial in accelerating vascular repair and limiting post PTCA restenosis, a major complication affecting prognosis. Netrin-1 potently attenuates vascular smooth muscle cell migration and proliferation, hallmarks of neointimal formation and restenosis. Therefore, netrin-1 is a superior cardioprotective agent that is much more than just a NO generator, or a superoxide suppressor, or a gene expression regulator, or a mitochondrial protector, or a survival signal, or a repair promoter. It is uniquely a combination of all these features that is not paralleled by anything else known to the scientific literature or the current drug development for acute myocardial infarction therapy. In addition, as shown by data in this section 1 and section 3 below, both pre-conditioning and post-conditioning treatments of netrin-1 is highly potent in exerting cardioprotective effect ex vivo and in vivo. In practice this means netrin-1 can be used both preventively and therapeutically. This also makes netrin-1 a unique treatment option. Taken together, the data herein show that netrin-1 can be used for acute treatment of myocardial infarction with the advantage of also preventing chronic complications such as procure-induced restenosis. The effects of netrin-1 on vascular injury and repair also have broad application to other vascular diseases such as atherosclerosis and hypertension in which the process is initiated at least partially by an endothelial cell damage and/or vascular smooth muscle dysfunction.

2. Netrin-1 Exerts Cardioprotection Via Attenuation of NADPH Oxidase Isoform 4, NOS Uncoupling and Mitochondrial Dysfunction Oxidative stress has been shown to mediate cardiac ischemia reperfusion (I/R) injury. As provided above, netrin-1 induces cardioprotection at least partially via a DCC/ERK1/2-dependent nitric oxide (NO) production and its in vivo protective effects are shown using a classic coronary artery ligation model of I/R. As disclosed herein, netrin-1 also regulates the oxidative stress pathways. Thus, it was hypothesized that netrin-1 protects the heart partially via the attenuation of superoxide production derived from NADPH oxidase (NOX) and uncoupled NO synthase (NOS) and that I/R induces mitochondrial damage through a NOX/NOS uncoupling/mitochondria pathway. To this end, hearts rapidly removed from 5-7 weeks old C57BL6 mice were perfused using a Langendorff system, and subjected to a 20 minute global ischemia, followed by a 60 minute reperfusion. Total superoxide production measured with electron spin resonance (ESR) shows about a 2.5 fold increase in I/R-injured hearts compared with controls (p<0.001), which was eliminated by netrin-1 perfusion to baseline. The expression level of NOX proteins as a possible source of superoxide were examined and it was found that NOX4 was increased by about 1.7 fold in I/R-injured hearts compared to controls, with netrin-1 reducing this overexpression to about 1.27 fold. Analysis of L-NAME sensitive superoxide production, an indicator of NOS (un)coupling activity, revealed that NOS was uncoupled by I/R, and recoupled by netrin-1 perfusion. It was further found that siRNA-mediated NOX4 silencing was able to recouple NOS, reduce infarct size, and improve mitochondrial function. Finally, recoupling of NOS with sepiapterin was also effective in reducing infarct size and improving mitochondria function in I/R-injured heart. In summary, this data demonstrate a novel pathway for netrin-1's cardioprotective effect, namely from a reduction of NOX4 expression, to the restoration of NOS function, to improving mitochondrial function and ultimately decrease in infarct size resulting from I/R injury. Thus, netrin-1 abrogates ischemia reperfusion induced mitochondrial dysfunction in the heart via attenuation of NOX4 and NOS uncoupling.

As provided above, the cardioprotective effects of netrin-1 is partly mediated via an increase in the production of nitric oxide (NO) via a novel DCC/ERK1/2/NOS pathway. However, it was unknown whether other species, such as superoxide which can form the cytotoxic peroxynitrite in the presence of NO, is involved in cardioprotection.

Thus, the effects of netrin-1 on superoxide production and mitochondrial function in relation to cardioprotection against I/R injury was studied using the Langendorff preparation. Two different sources of superoxide, namely NADPH oxidases and uncoupled NOS, were examined. It was found that I/R induced an increase in superoxide production, which was eliminated with netrin-1 perfusion. It was also shown that the NADPH oxidase isoform 4 (NOX4) was upregulated in the FR-injured heart. Since NOX lies upstream of NOS uncoupling, the coupling state of NOS in the FR-injured heart was studied and it was found to be uncoupled and restored with netrin-1. A siRNA technique to reduce the expression of NOX4 was used and it was found that reducing the expression of NOX4 has similar cardioprotective effects as netrin-1 perfusion. The NOX siRNA approach was also effective in preventing I/R induced NOS uncoupling and mitochondrial dysfunction. Lastly, it was found that perfusing hearts with sepiapterin, an agent known to recouple eNOS, protects against injury by improving mitochondrial function. Thus, these results suggest a second pathway of NOX4/NOS/mitochondria involved in the cardioprotective effect of netrin-1 against I/R injury.

EXPERIMENTS: Unless otherwise noted, all chemicals and drugs were obtained from Sigma-Aldrich (St. Louis, Mo.) in highest purities. Custom made siRNA was obtained from Integrated DNA Technologies (Coralville, Iowa).

Animals: 6-8 week old male C57BL/6J mice were obtained from Jackson Laboratories (Bar Harbor, Me.). Animals were housed in a pathogen free facility, with free access to food and water, and under a 12-hour light/dark cycle. The use of animals and experimental procedures were approved by the Institutional Animal Care and Usage Committee at the University of California Los Angeles.

Langendorff perfusion: Animals were initially anesthetized with isoflurane. Hearts from the animals were rapidly removed and transferred to ice cold modified Krebs-Henseleit buffer (KHB), consisting of (in mmol/L): NaCl 118.0, KCl 4.7, $CaCl_2$ 2.5, $MgSO_4$ 1.2, $KH_2PO_4$ 1.2, $NaHCO_3$ 25.0, Glucose 10, pH 7.35. After clearing the heart from surrounding tissue, the aorta was cannulated with a 20-gauge stainless steel blunt need, transferred to a Langendorff apparatus, and perfused with modified KHB prewarmed to 37° C. and bubbled with 95%/5% $O_2/CO_2$. While under perfusion, the heart is kept in a 37° C. chamber.

Figure 11A:
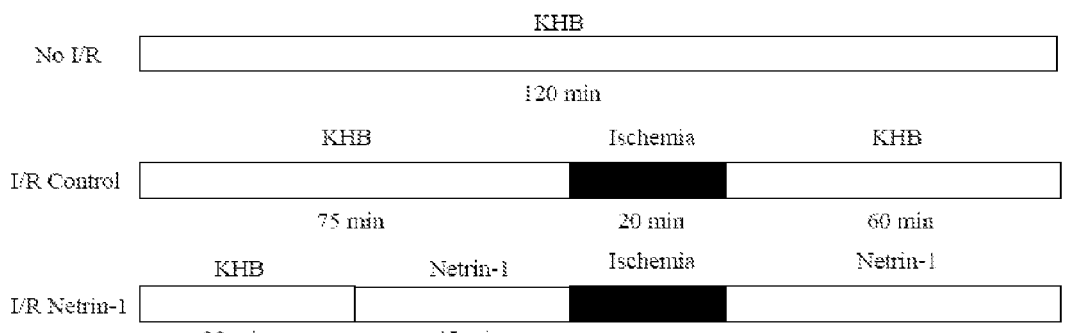
FIGS. 11A and 11B evidence that netrin-1 attenuates I/R induced superoxide production.

For no I/R, hearts were perfused with KHB for 120 min. For I/R, hearts were perfused with KHB for 75 min, perfusion was stopped for 20 minutes for ischemia, and finally reperfused for 60 min. For I/R with netrin-1, hearts were perfused with KHB for 30 min, followed by 45 min of perfusion with netrin-1 (100 ng/ml), 20 min ischemia, and 60 min of reperfusion. These treatment protocols are illustrated in FIG. 11A.

TTC staining: At the end of the Langendorff experiments, hearts were removed and sliced into 6 sections. Heart tissue was then incubated in a TTC solution (1% TTC in PBS) for 20 min at 37° C. Hearts were then stained overnight in 10% formalin for contrast.

Preparation of heart tissue for biochemical assays: At the end of the Langendorff experiment, hearts were removed from the perfusion apparatus and immediately transferred onto ice awaiting homogenization. For superoxide measurement and Western blot analysis, hearts were homogenized with ice cold homogenization buffer (Tris 50 mmol/L, EDTA 0.1 mmol/L, EGTA 0.1 mmol/L, protease inhibitor cocktail, pH 7.4) on ice using a glass homogenizer. For Western blot analysis, the supernatant from the homogenate centrifuged at 13,000 rpm for 15 min at 4° C. was used.

Superoxide measurements with electron spin resonance (ESR): Superoxide production was measured from heart homogenates using ESR as previously described. Briefly, heart homogenate (10 μg) was mixed in a spin trap solution (CMH, 0.5 mmol/L), loaded into a glass capillary (Fisher Scientific) in the presence or absence of L-NAME (100 μmol/L), and assayed for superoxide using a Bio-Spin ESR spectorphotometer (Bruker) at the following settings: center field 3476; sweetp width 9G; frequency 9.75 GHz; microwave power 21.02 mW; modulation amplitude 2.47 G; 512 points resolution; receiver gain 1000.

Western blot: Western blotting was performed as per standard protocols. Primary antibody for NOX4 (Abcam, Cambridge, Mass.) was used at a dilution of 1:1000. Primary antibody for actin (Sigma-Aldrich, St. Louis, Mo.) was used at a dilution of 1:3000. Secondary antibody conjugated to HRP (Bio-Rad, Hercules, Calif.) was used at a dilution of 1:2000 for NOX4, and 1:10000 for actin.

Mitochondria isolation: Heart tissue was rinsed twice in ice cold PBS immediately after the end of the Langendorff experiment. The tissue was then homogenized in a pre-chilled glass homogenizer using isolation buffer I (sucrose 250 mM, EGTA 1 mM, HEPES 10 mM, and Tris-HCl 10 mM, pH 7.4, 1 ml buffer/0.1 g tissue) on ice. The homogenate was then centrifuged at 800 g for 7 min at 4 C. The supernatant was then transferred to a new tube and centrifuged at 4000 g for 15 min at 4° C. The pellet was rinsed using 1 ml of isolation buffer II (sucrose 250 mM, HEPES 10 mM, Tris-HCl 10 mM, pH 7.4), then centrifuged again at 4000 g for 15 min at 4° C. Further purification was performed by resuspending the pellet with 3 ml of a 19% percoll solution, then layering this on top of a double layer of 30% and 60% percoll solution in a centrifugation tube. The entire tube was spun for 60 min at 1,000 g. The mitochondria layer in the tube was carefully removed. Percoll was washed from the sample by alternating centrifugation and resuspension with isolation buffer II. The final pellet was resuspended in isolation buffer II.

Mitochondrial swelling assay: 30 μg of freshly isolated mitochondria were mixed in a buffer containing 250 mM sucrose and 10 mM Tris (pH 7.4). The mixture was then incubated with 5 mM succinate for 1 minute at room temperature, then with 250 μM of $CaCl_2$. Absorbance at 540 nm was measured immediately for 20 min at 1 minute intervals. Swelling was measured as a decrease in absorbance over time.

siRNA treatment: A nanoparticle based in vivo transfection kit (Altogen Biosystems) was used to deliver NOX4 siRNA into animals. 5 nmol of in vivo grade siRNA (sense: CAUGCUGCUGCUGUUGCAUGUUUCA (SEQ ID NO:19), antisense: CCCUCUGAUGUAAUGGAACUC-CGUA (SEQ ID NO:20), Dharmacon) was prepared with the transfection kit as per manufacturer's instructions. Injections were made via the tail vein. One injection per 24 hrs was made for a total of 2 injections. Experiment was performed 24 hrs after the last injection.

In vivo model of ischemia reperfusion injury: Male mice (9-12 wks of age) were subjected to myocardial ischemia reperfusion injury as previously described in detail. In brief, mice were anesthetized with sodium pentobarbital (50 mg/kg body wt i.p.), the depth of anesthesia was verified by recurrent testing of the palpebral reflexes and hind paw withdrawal throughout the experiment. Furthermore, rectal body temperature was continuously measured and maintained at 36.5±1° C. After left fourth thoracotomy and pericardiotomy, the heart was exposed, whereas a suture (8-0) was looped under the left anterior descending coronary artery 1-3 mm from the tip of the normally positioned left atrium. A 30-min coronary artery occlusion was induced by ligation of the suture (a 1 to 2 mm section of PE-10 tubing was placed between the suture and the artery to prevent damage to the vessel), subsequent removal of the suture instated coronary reperfusion, followed by closure of the chest. After 24 hrs of reperfusion, the heart was excised and postmortem perfused as previously described. The area at risk (AAR) was delineated by perfusion with a 1% solution of Evans blue; myocardial infarct size was determined by perfusion with a 1% solution of 2,3,5-triphenyltetrazoliumchloride (TTC) in phosphate buffer (pH 4.4, 37° C.). Infarct size was measured by planimetry (Adobe Photoshop, Adobe Systems Incorporated, San Jose, Calif.) and expressed as a percentage of the AAR. Mice in the respective experimental groups either received an intravenous bolus dose of Netrin-1 (5 µg/kg, 24 hrs prior to ischemic ligation) or PBS (vehicle). Ischemic injury was elicited 24 hrs later by a 30-min coronary artery occlusion, followed by 24 hrs of reperfusion.

Statistical analysis: All statistical analysis was performed using Sigmastat (Systat). Data presented as mean±SEM. Student's t-test was used when comparing two groups. ANOVA was used to compare multiple groups. Holm-Sidak test was used as the post-hoc test after the ANOVA. Signficance level was set to be 0.05.

Results

Figure 11B:
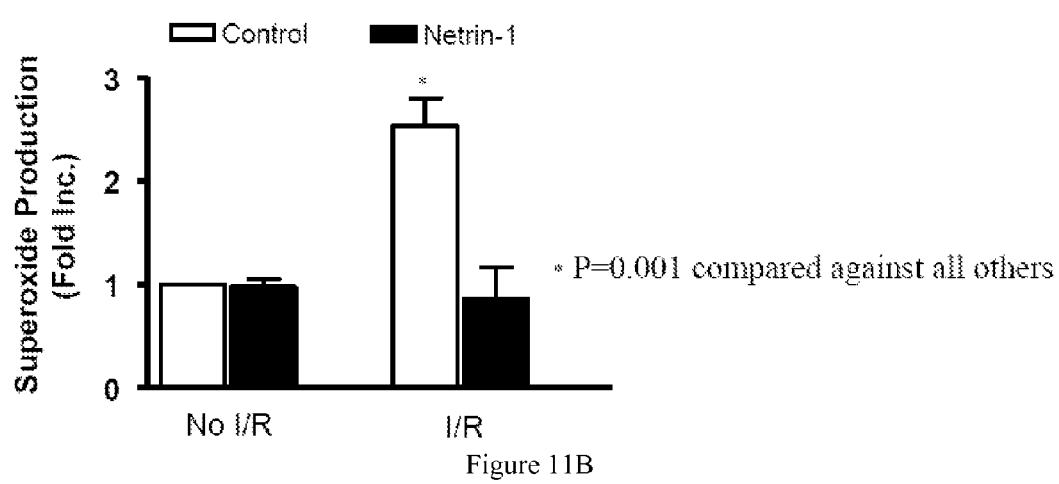

Netrin-1 abolishes FR-induced increase in superoxide production: To determine whether superoxide plays a role in I/R induced cardiac damage, superoxide production using ESR on heart homogenates from hearts that underwent I/R injury using the Langendorff model, with and without infusion of netrin-1 (n=3 for all conditions) was examined. As shown on FIG. 11B, I/R injury induced about a 2.5 fold increase in superoxide production compared to non I/R controls (P=0.001). Perfusion with netrin-1 reduced this increase back to baseline levels.

Figure 12:
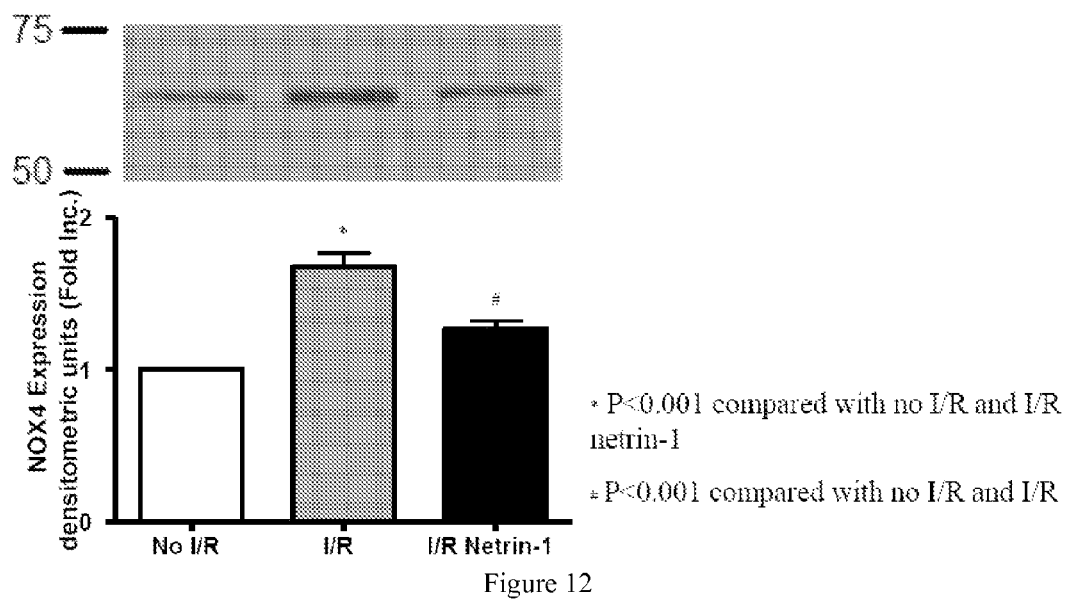
FIG. 12 evidences that netrin-1 attenuates FR-induced NOX4 upregulation. The top panel shows a representative Western blot of NOX4 from whole heart homogenate, while the bottom panel shows the summarized data (n=4 each group). NOX4 expression from I/R was significantly higher than both no I/R and I/R netrin-1 (p<0.001, ANOVA with Holm-Sidak).

NOX4 is upregulated in I/R-injured hearts but attenuated by netrin-1: One of the possible sources of the FR-induced increase in superoxide production is NADPH oxidases (NOX). Expression of NOX4 using Western blot analysis shows that NOX4 was upregulated in I/R (FIG. 12, n=4 for each condition, p<0.001). Further, this upregulation was reduced in netrin-1 perfused I/R hearts, suggesting that netrin-1 exerts its cardioprotective effects, at least partially, via preventing the upregulation of NOX4. The other NOX isoforms including NOX1 and NOX2 were however unaffected by I/R or netrin-1. NOX3 and NOX5 expression was undetectable in the heart.

Figure 13:
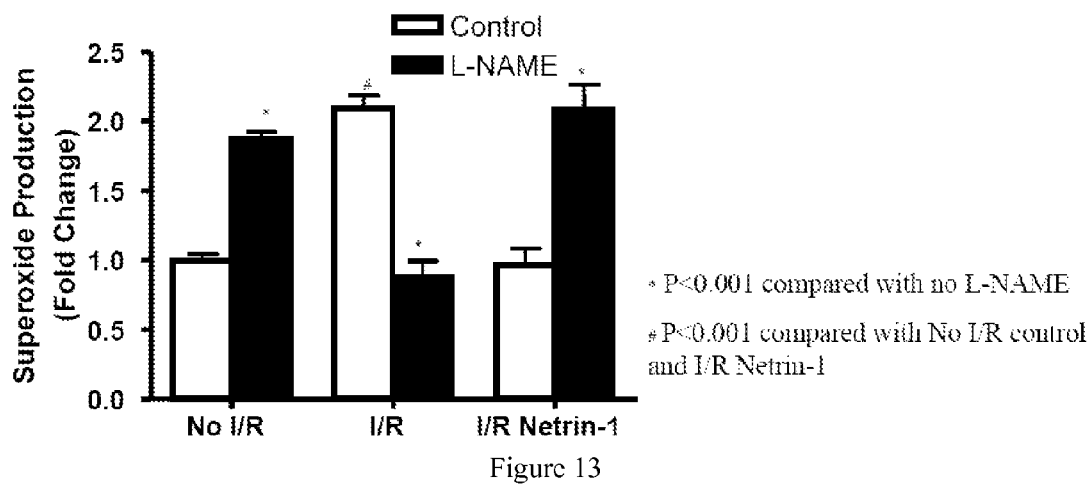
FIG. 13 shows that netrin-1 attenuates FR-induced NOS uncoupling. Superoxide production was measured using ESR and then normalized to control and no I/R condition (n=5 each). The addition of L-NAME in samples that have functional or coupled NOS will increase the production of superoxide, such as in the no I/R case. However, in samples with uncoupled NOS, the production of superoxide will decrease, as shown here in I/R condition. Perfusion with netrin-1 during I/R, as shown on the right, recouples NOS as evident by the increase in ESR measured superoxide production with the addition of L-NAME. Multiple comparisons by ANOVA, with Holm-Sidak post-hoc.

Netrin-1 attenuates I/R induced NOS uncoupling: To assess the coupling state of NOS under I/R and netrin-1-infused I/R conditions, superoxide production was measured with and without the addition of L-NAME, a general inhibitor of NOS. Under normal conditions when NOS is coupled, it produces nitric oxide (NO). Therefore, the addition of L-NAME will reduce the level of NO, resulting in an increase in measured superoxide production. On the other hand, if NOS is uncoupled and is producing superoxide, the addition of L-NAME will reduce measured superoxide. Hence, the direction of change between superoxide measurement with and without the addition of L-NAME can be used to assess the coupling state of NOS. Using this method, the coupling state of whole heart homogenate from each condition was measured (n=5 each condition), with the results shown in FIG. 13. Under I/R condition, the addition of L-NAME significantly decreased the level of superoxide production (P<0.001), which suggests that under I/R condition, NOS is uncoupled.

With the case of I/R perfused with netrin-1, the addition of L-NAME in the measurement significantly increased superoxide production (P<0.001), suggesting that NOS is recoupled.

Figure 14A:
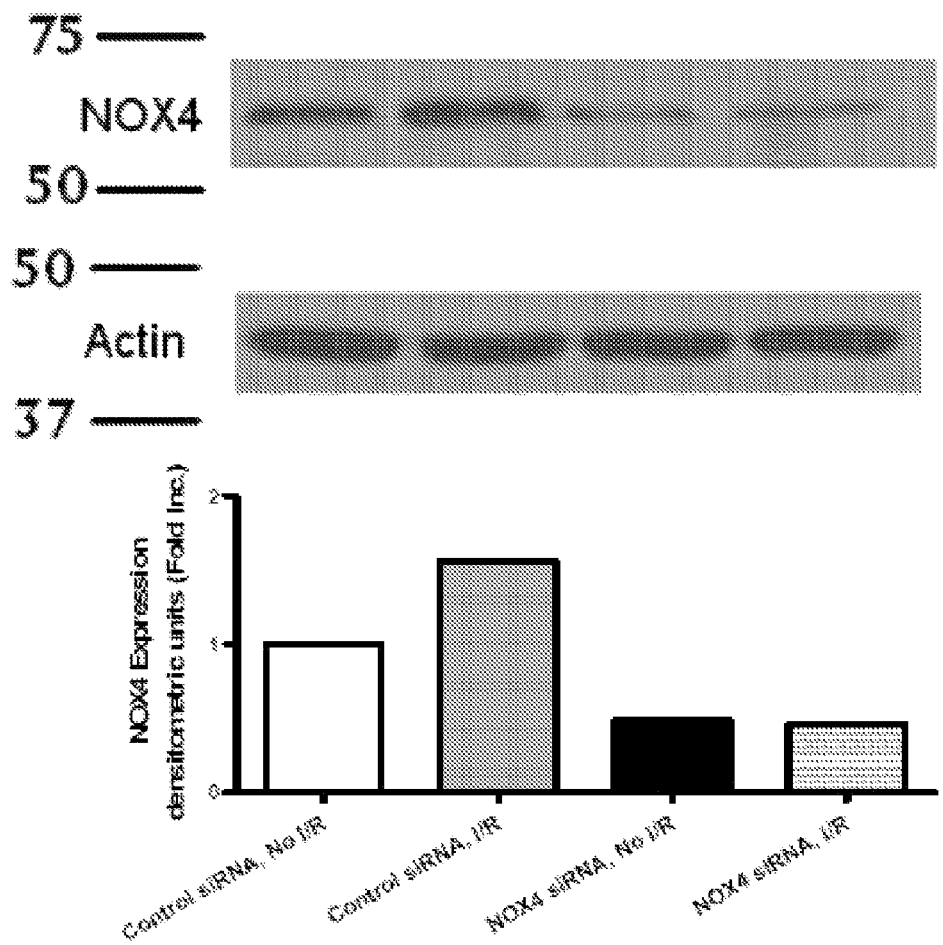
FIGS. 14A-14D evidence that NOX4 siRNA treated mice exhibit protection against I/R injury.

Effects of siRNA silencing NOX4 expression on NOS uncoupling, mitochondrial dysfunction, and infarct size: Since netrin-1 seems to exert its protective effect at least partially via the attenuation of NOX4 and subsequent eNOS uncoupling, the expression of NOX4 in vivo was reduced using siRNA to replicate this protection. The Western blot of FIG. 14A shows that siRNA injection was effective in reducing the expression of NOX4 in the hearts. Further, this reduction prevented the NOX4 expression increase during I/R as compared to hearts treated with control siRNA.

Figure 14B:
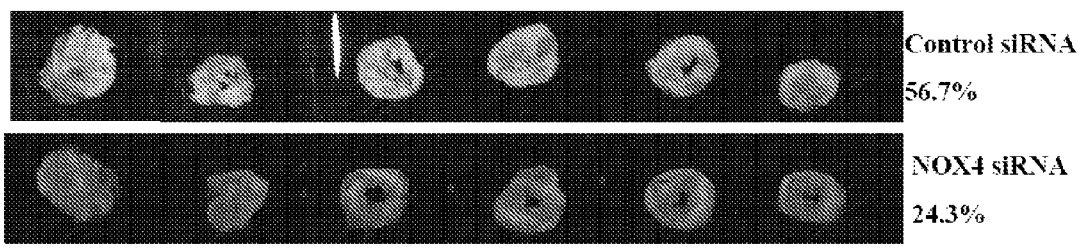
Figure 14C:
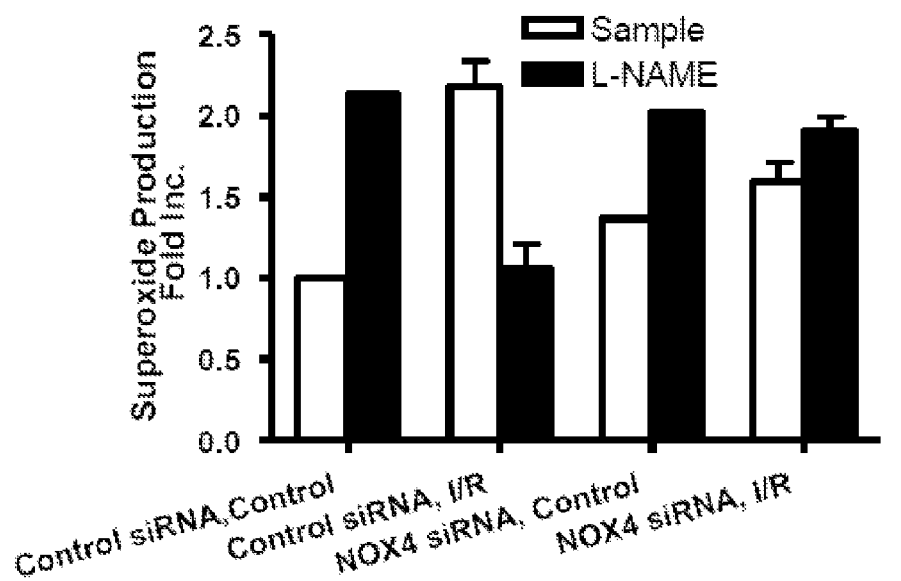
Figure 14D:
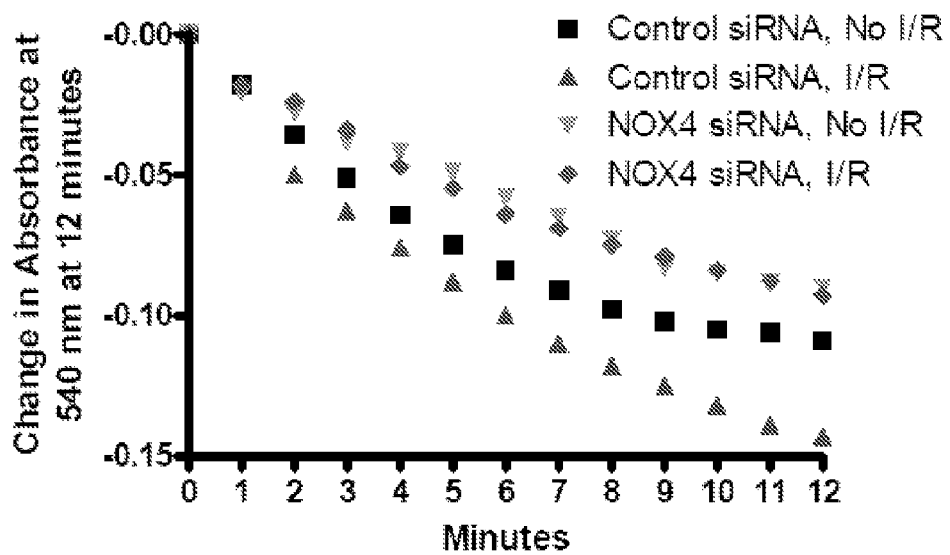

Using this siRNA technique, whether the decrease in NOX4 expression confers protection again I/R injury was assessed. FIG. 14B shows TTC sections from siRNA treated hearts subjected to I/R, which clearly shows that hearts deficient in NOX4 was protected against I/R injury. The NOS coupling state using ESR superoxide measurements was determined and FIG. 14C shows that hearts from animals treated with control siRNA are in the same NOS coupling state as untreated animals. On the other hand, animals treated with NOX4 siRNA showed functional NOS under I/R. Further, when mitochondria function was assessed using mitochondria swelling assay, hearts from siRNA treated animals shows a marked improvement in mitochondria function (FIG. 14D). This data suggests that NOX4 plays a major role in exacerbating I/R damage, at least partially via the recoupling of NOS and prevention of mitochondrial dysfunction.

Figure 15A:
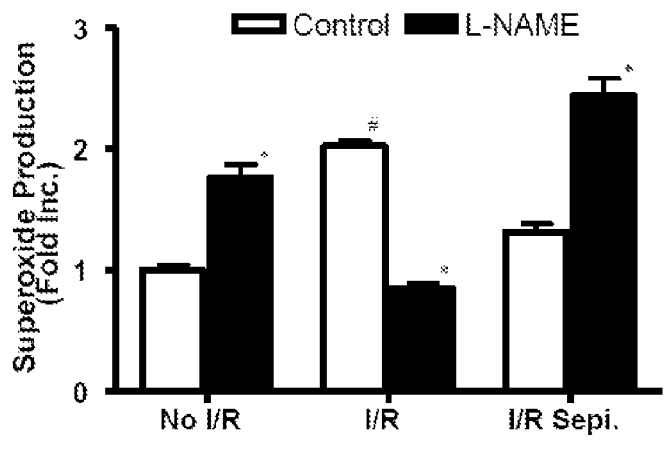
FIGS. 15A and 15B evidence that recoupling of NOS with sepiapterin induces mitochondrial protection.
Figure 15B:
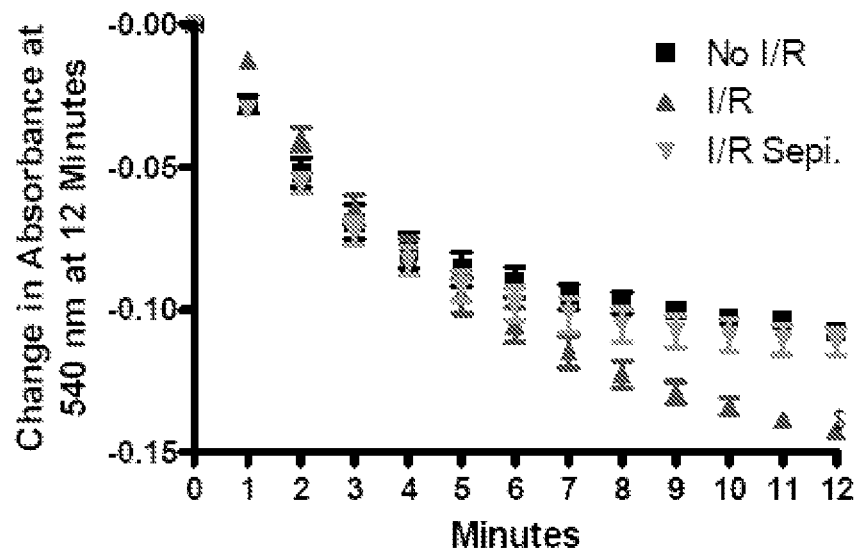

Sepiapterin recouples NOS, protects against IR damage, and improves mitochondria function: As provided above, netrin-1 exerts its cardioprotective effects at least partially via the attenuation of NOX4 and subsequently improving NOS function. Thus, whether the improvement of NOS function by itself is sufficient for the protection of I/R injury was determined. Hearts with perfused with sepiapterin, a precursor for tetrahydrobiopterin (H4B), to improve H4B levels, which is generally deficient when NOS is uncoupled (n=4 for each condition). FIG. 15A shows the result from L-NAME sensitive superoxide production measured via ESR, which shows that sepiapterin perfusion was effective in recoupling NOS. Next, mitochondria function was assessed using a mitochondria swelling assay on isolated mitochondria from the perfused hearts. The data on FIG. 15B shows that with I/R (▲) mitochondria function was reduced compared to control (■) (P=0.006). Sepiapterin perfusion (▼) restored mitochondria function. This suggests that the improvement of NOS function by itself is sufficient for the protection of the heart from I/R injury, showing the importance of NOS function in the development of I/R damage.

Figure 16:
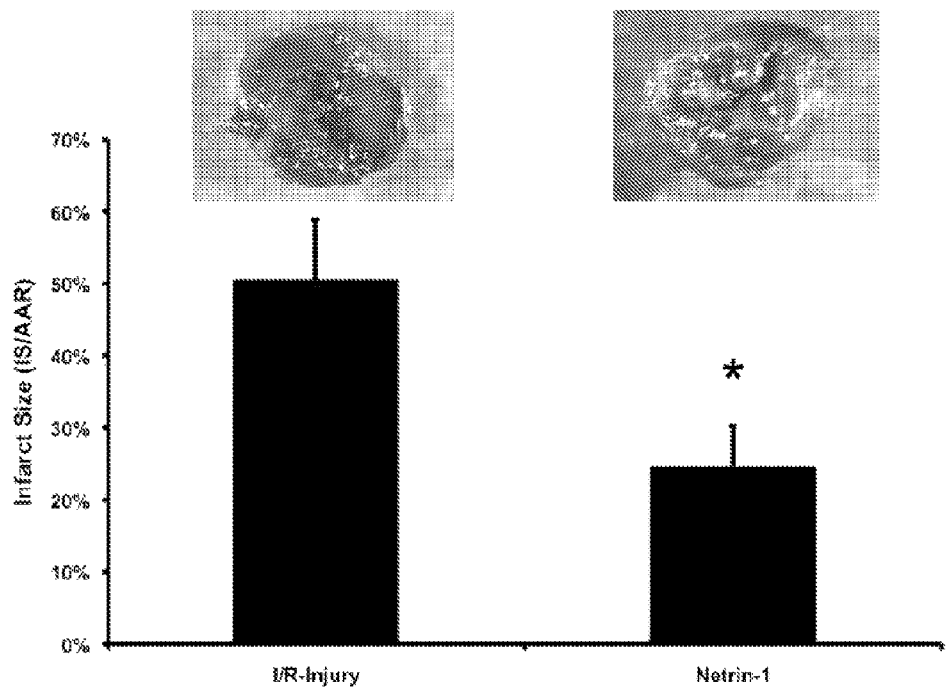
FIG. 16 demonstrates that netrin-1 when given in vivo, markedly attenuated infarct size. Netrin-1 was tail vein injected into mice at 5 μg/kg 24 hrs prior to an in vivo model of ischemia reperfusion on day 2 that is achieved by 20 min coronary occlusion and 24 hr reperfusion. On day 3, the mouse hearts were harvested by first injecting evans blue to label risk area, and then subjected to TTC staining for infact size. P<0.05, n=4, t-test.
Figure 17:
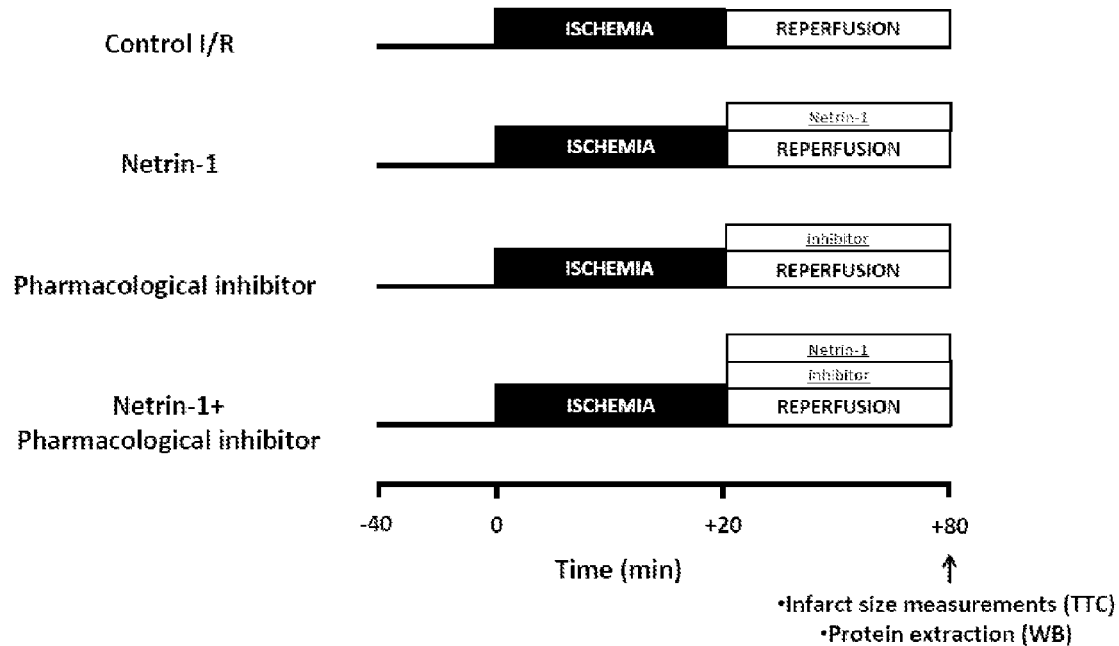
FIG. 17 diagrammatically provides the experimental protocols of the isolated C57BL/6J WT, DCC +/+ and +/−mice heart experiments with netrin-1 added post-conditionally. Data included in up to FIG. 16 indicated preventative role of netrin-1 in cardiac I/R injury when netrin-1 was given pre-conditionally (prior to reperfusion). These new set of experiments are however critical in understanding if netrin-1 exerts cardioprotective effects when delivered as a post-conditioning agent at the onset of reperfusion (i.e. together with PTCA procedure). All hearts were stabilized for 40 min prior to experiments. Control hearts received 20 min of global no-flow ischemia followed by 60 min of reperfusion. Netrin-1 was given at the onset of the reperfusion. The signaling pathway inhibitors were given either alone accordingly or with the netrin-1 treatment. The arrows indicate the time for myocardial infarct sizing with 2,3,5-TTC (TTC) and for protein analysis by Western blot (WB). ■=global no-flow ischemia.
Figure 18:
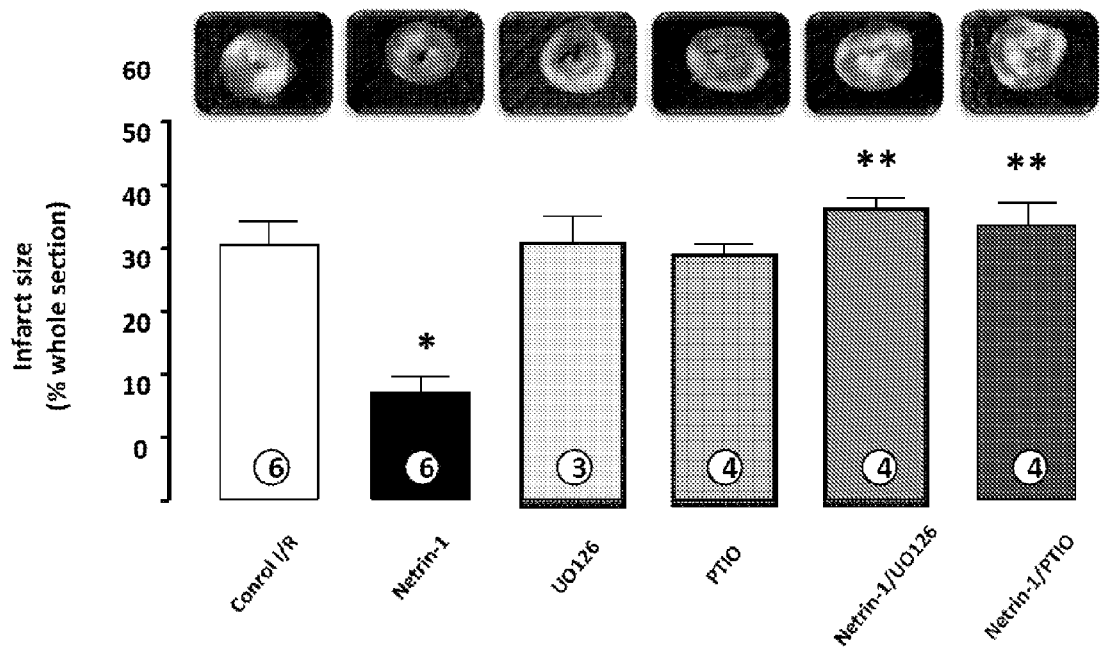
FIG. 18 provides the myocardial infarct size obtained with the isolated C57BL/6J WT mice hearts experiments. Drugs were given as depicted in FIG. 17. Netrin-1 post-conditioning resulted in a significant reduction in infarct size, which could be abolished with the co-treatment of pharmacological inhibitors of known protective signaling elements. [2-phenyl-4,4,5,5-tetramethylimidazoline-1-oxyl 3-oxide (PTIO)=nitric oxide scavenger and U0126=ERK blocker]. PTIO and U0126 alone had no effect on infarct size. Infarcts size was calculated as percentage of the risk area. *p≤0.05 vs. Control I/R, **p≤0.05 vs. Netrin-1. These data indicate that netrin-1 can serve as an effective treatment of ischemic heart at the early stage of reperfusion therapy in subjects with myocardial infarction, and this is mediated by a DCC/ERK/NO pathway (this figure and FIG. 19).
Figure 19:
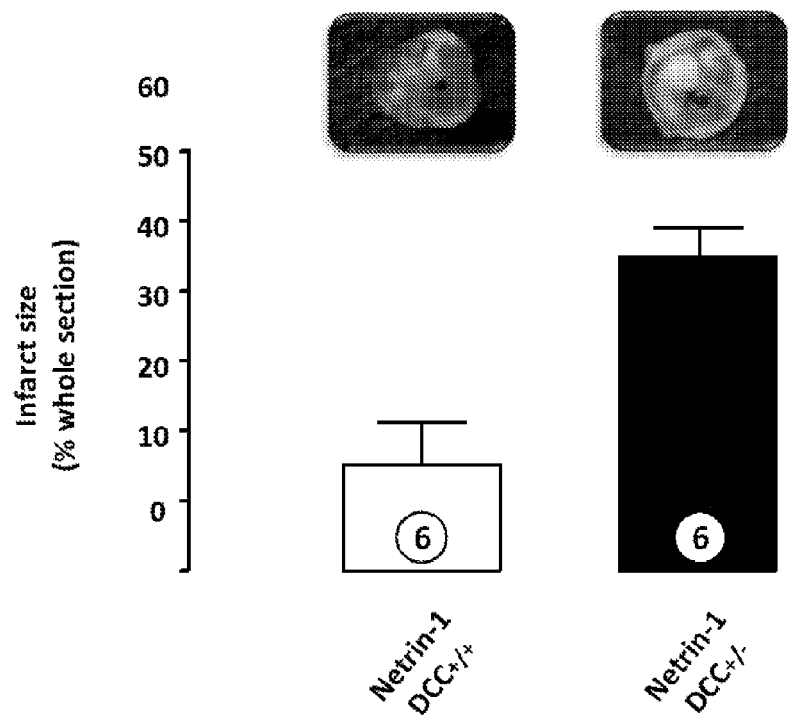
FIG. 19 provides the myocardial infarct size obtained with the isolated C57BL/6J DCC +/+ and +/−mice hearts experiments. Netrin-1 was given as depicted in FIG. 17. Netrin-1 resulted in a significant reduction in infarct size, which is abolished in DCC +/−mice. Infarcts size was calculated as percentage of the risk area. *p≤0.05.
Figure 20:
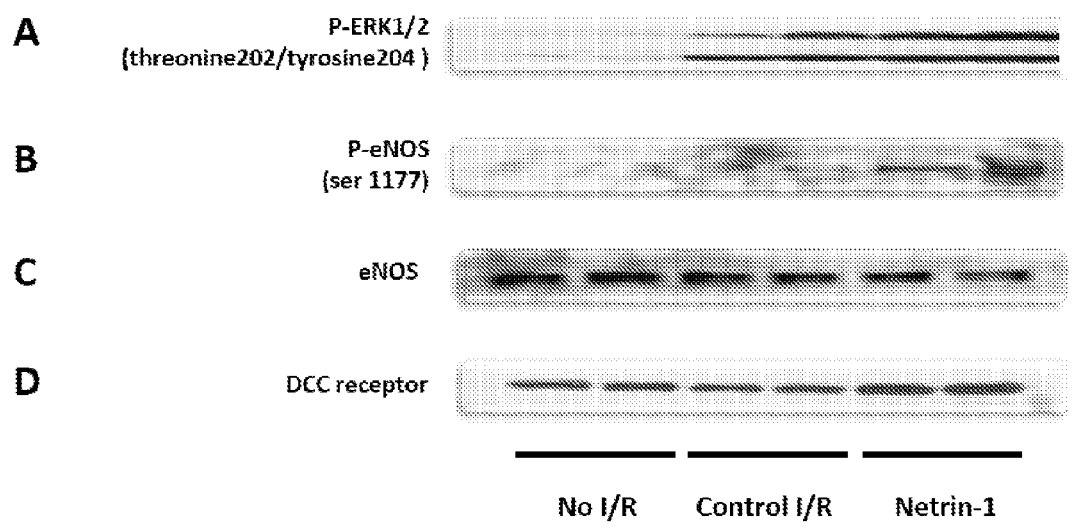
FIG. 20 provides representative Western blots of P-ERK1/2 (panel A), P-eNOS (panel B), eNOS (panel C), and DCC receptor (panel D) expression in isolated mouse heart. Myocardial samples were obtained at 60 min of reperfusion following a 20 min period of no-flow global ischemia as indicated by the arrows in FIG. 17.

Netrin-1 perfusion induces cardioprotection in vivo: As provided in FIG. 16, netrin-1 treatment markedly reduced infarct size from a classic in vivo model of I/R injury (details see methods section).

3. Netrin-1 is Cardioprotective when Administered at the Onset of or after Reperfusion As provided above, when prophylactically administered, netrin-1 markedly reduces myocardial injury after ischemia reperfusion (I/R). Thus, the following experiments were conducted to determine whether netrin-1 is also cardioprotective against I/R if administered at the onset of or after reperfusion.

EXPERIMENT

Langendorff perfused hearts isolated from C57BL/6J wild-type (WT) control mice or DCC +/− mice underwent 20-min of global ischemia followed by 60-min of reperfusion. DCC (deleted in colorectal cancer) is one of the netrin-1 receptors we found to be however specifically involved in netrin-1 preconditioning induced cardioprotection. Netrin-1 was infused postconditionally at the onset of reperfusion at 100 ng/mL concentration with and without U0126, a specific MEK1/2 inhibitor, or 2-Phenyl-4,4,5,5-tetramethylimidazoline-1-oxyl-3-oxide (PTIO), a nitric oxide (NO)-scavenger. Infarct size was determined to evaluate the severity of myocardial injury using TTC staining, and protein kinase activations determined by Western blot analysis.

Results

In WT mice, netrin-1 postconditioning significantly reduced infarct size to 17±2.5% from 40.5±4.2% in the untreated control I/R group). U0126 or PTIO administration alone had no effect on infarct size but abolished the effects of netrin-1, implicating intermediate roles of MEK/ERK1/2 and NO. Indeed, eNOS and ERK1/2 phosphorylations were both upregulated by netrin-1 treatment. The protective effect of netrin-1 was markedly diminished in the DCC +/−mice (infarct size increased to 44.5±2% from 15±2.6% in the DCC +/+group), indicating a dependency on DCC. Netrin-1 also feed-forwardly upregulated DCC protein expression.

These results strongly suggest that netrin-1 acts as a postconditioning mimetic by increasing NO production via activation of ERK1/2/eNOS pathway, which also involves DCC activation and upregulation. These findings indicate that netrin-1 may be used as a clinically relevant agent for acute treatment of myocardial infarction.

Here we present novel findings that netrin-1 acts as a postconditioning mimetic by increasing NO production via activation of ERK1/2/eNOS pathway, which also involves DCC activation and upregulation. These findings indicate that netrin-1 may be used as a clinically relevant agent for acute treatment of myocardial infarction.

4. Netrin-1 Inhibits Neointimal Formation Using a Femoral Artery Injury Model and Prevents Mobilized Endothelial Progenitor Cells (EPCs) from Apoptosis.

It was found that netrin-1 inhibits neointimal formation using a femoral artery injury model and prevents mobilized endothelial progenitor cells (EPCs) from apoptosis. Thus, netrin-1 exhibits beneficial effects on vascular repair, including EPC-mediated vascular repair. In addition, based on the neointimal results netrin-1 may also inhibit restenosis, which is a major complication of percutaneous transluminal coronary angioplasty (PTCA) treatment of myocardial infarction.

EXPERIMENTS

Femoral artery injury model for studies of vascular repair/neointimal formation: Femoral artery tissue was stained with Trichrome. An osmotic pump was implanted into animal (WT or DCC, about 6 months old) to give either vehicle or netrin (15 ng/day) 2 days prior to femoral injury. Femoral injury was performed on the right femoral artery. Sham surgery was performed on the left femoral artery. Both femoral arteries were harvested after 12 days.

Osmotic pump surgery: Animals were anesthetized in a closed chamber with isoflurane (about 5%), then rapidly moved to a nose cone supplying 95%:5% $O_2:CO_2$ mixed with 1.5% isoflurane to maintain the anesthetic state. Hair was removed from between the shoulder blades and behind the head with a hair removal gel (Nair), then disinfected with an iodine solution (Betadine). A small incision was made on the surface skin, and an osmotic pump (Alzet, model 2002) was inserted subcutaneously to the right flank. The wound was then closed with surgical clips.

Femoral injury surgery: Animals are anesthetized in a closed chamber filled with isoflurane (about 5%), then quickly moved to a nose cone supplied with 95%:5% $O_2:CO_2$ mixed with 1.5% isoflurane. After checking for proper anesthesia, the animal is turned on its back and restrained using surgical tape. Hair on the thigh area is removed using a hair removal lotion (Nair), then disinfected using an iodine solution. An incision is made on the right thigh area above the femoral artery. The femoral artery is then isolated and cleared of connective tissue. Blood flow is temporarily stopped using a small artery clamp, and an incision is made on a branch off the main artery near the knee. A fixed core wire guide (Cook, model C-SF-15-15) coated with heparin is inserted into the artery and advanced to the clamp. The artery clamp is then removed and the wire advanced until the femoral branch in the aorta. The wire is then allowed to stay for 30 seconds, then pulled back slowly towards the incision point. This insertion and pulling back is repeated for a total of 3 runs. At the end of the third run, the artery is once again clamped and the wire guide pulled free of the artery. The incision site on the artery is then ligated using surgical silk (5-0). The skin is then closed and sutured together (Vicryl, 6-0), then sealed with surgical glue. A similar procedure is preformed on the left leg, with the exception that the wire is not inserted into the artery.

Sample collection: At the end of the experimental period, animals were euthanized in a gas chamber with $CO_2$. The femoral artery was carefully isolated from connective tissue, rapidly removed from the body, and washed twice in ice cold PBS. Sample preparation: Samples were fixed in formalin overnight, then washed in water followed by 70% ethanol. The tissue was then given to the TPCL facility for paraffin embedding and sectioning at 4 microns.

Trichrome: Trichrome staining kit was used from Sigma-Aldrich (St. Louis, Mo.). Samples were first de-paraffinized and hydrated by washing in these solutions for 2×5 mins: xylene, 100%, 90%, 70% ethanol. Then, samples were washed under running tap water for 10 min, then washed in DI water for 5 min. Samples were then placed in Bouin's solution overnight at RT. The next day, the slides were washed in running tap water for 10 min, then 5 min in working Weigert's Iron Hematoxyline solution, then 5 min in running tape water, then rinsed in DI water, then 5 min in Biebrich Scarlet-acid Fucshin, then rinsed in DI water, then 5 min in working phosphotungstic/phosphomolybdic acid solution, then 5 min in aniline blue solution, then 2 min in 1% acetic acid. Samples were then washed in running tap water for 5 min, then dehydrated by washing in 2×5 min in: 70% ethanol, 90% ethanol, 100% ethanol, xylene. Slides were then mounted with permount.

Netrin-1 protection of endothelial progenitor cells apoptosis—important for EPC-mediated vascular repair: Netrin-1 pretreatment (100 ng/ml) was found to substantially attenuate hydrogen peroxide (500 μmol/L, 30 min) induced apoptosis of EPCs (56% down to 14% for dead cells, FIG. 25). EPC survival and homing to the injured vascular bed is critical for rapid repair and prevention of neointimal formation and restenosis.

TUNEL apoptosis assay BM-EPC: bone marrow derived EPCs were isolated and that single colony cells were used for experiments. See FIG. 25B. The well characterized and confluent cells were subjected to the treatment protocol above (pretreatment with netrin-1 at 100 ng/ml for 30 min prior to treatment with hydrogen peroxide at 500 μmol/L for 30 min) and then TUNEL apoptosis assay using a kit from Chemicon International, Inc. (Billerica, Mass.).

As provided above, data indicate that netrin-1 markedly attenuated hydrogen peroxide (reactive oxygen species important for damage) induced EPC apoptosis.

Methods of treating, inhibiting or reducing I/R injury of cardiac tissue according to the present invention include administering a therapeutically effective amount of a composition comprising netrin-1 to the cardiac tissue before, during, or after being subjected to conditions which cause the I/R injury.

Administration of netrin-1 protein can be accomplished by direct administration of netrin-1, preferably human netrin-1. In some embodiments, administration of netrin-1 is accomplished by administering a nucleic acid which encodes netrin-1.

The term "therapeutically effective amount" as used herein is intended to mean an amount which is effective to alleviate, ameliorate or prevent a symptom or sign of a disease or condition to be treated. In some embodiments, a therapeutically effective amount is an amount which has a beneficial effect in a subject having signs and/or symptoms of I/R injury of cardiac tissue. In some embodiments, a therapeutically effective amount is an amount which inhibits or reduces signs and/or symptoms of I/R injury as compared to a control. Signs and symptoms of I/R injury to cardiac tissue are well-known in the art and include sudden chest pain (typically radiating to the left arm or left side of the neck), shortness of breath, nausea, vomiting, palpitations, sweating, and anxiety.

The amount of a composition of the present invention administered to a subject and the route of administration depends on factors such as the severity of an infection affecting the subject, the activity and rate of excretion of the netrin-1, and the general physical characteristics of the subject including age, gender and body weight. One of skill in the art may readily determine a therapeutically effective amount and route of administration in view of these and other considerations typical in medical practice. Therapeutically effective amounts of netrin-1 may be readily determined by those skilled in the art without undue experimentation.

In general, a therapeutically effective amount of netrin-1 ranges from about 0.001 mg/kg-100 mg/kg body weight, e.g. about 0.01-10 mg/kg to about 0.1-5 mg/kg. A therapeutically effective amount of netrin-1 may be manufactured and/or administered in single or multiple unit dose forms.

Compositions according to the instant invention include netrin-1 and a pharmaceutically acceptable carrier. The term "pharmaceutically acceptable carrier" as used herein refers to a carrier or diluent that is generally non-toxic to an intended recipient and which does not significantly inhibit activity of netrin-1 included in the composition. A composition according to the present invention generally includes about 0.1-99% of netrin-1.

In some embodiments, netrin-1 is included in a composition of the present invention in the form of a free acid or free base in particular embodiments. In some embodiments, netrin-1 is included in a composition in the form of a pharmaceutically acceptable salt such as an acid or base addition salt. A pharmaceutically acceptable salt refers to any salt form of netrin-1 that is generally non-toxic to an intended recipient and which does not significantly inhibit activity of the netrin-1 or other active agent included in the composition. In some embodiments, netrin-1 is provided in the form of a hydrate or a prodrug.

A composition including netrin-1 may be administered by a systemic route and/or by a local route. Suitable routes of administration illustratively include intravenous, oral, buccal, parenteral, intrathecal, intracerebroventricular, intraperitoneal, intracardiac, intraarterial, intravesicle, ocular, intraocular, rectal, vaginal, subcutaneous, intradermal, transdermal, intramuscular, topical, intranasal, and transmucosal.

In some embodiments, more than one form of netrin-1 may be provided in the methods and compositions of the present invention. Thus, for example, human netrin-1 and one or more variants of human netrin-1 or mouse netrin-1 are both included in a composition.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method of treating, inhibiting, or reducing an ischemia/reperfusion injury to a heart in a subject in need thereof, comprising administering a therapeutically effective amount of netrin-1 to the subject, thereby treating, inhibiting or reducing the ischemia/reperfusion injury.

2. The method of claim 1, wherein superoxide production in the heart is attenuated, NOX4 expression in the heart is attenuated, NOS uncoupling in the heart is reduced, NOS recoupling in the heart, nitric oxide production in the heart is increased, DCC-dependent activation of ERK1/2 and eNOS is stimulated, amount of loss of NO by the heart is reduced, NO production is increased in the heart, phosphorylation of ERK1/2 and/or eNOS is increased in the heart, loss of DCC protein and mRNA expression is reduced in the heart, superoxide production by the heart is reduced, cell apoptosis is reduced, or a combination thereof results from the administration of netrin-1.

3. The method of claim 1, which further comprises administering sepiapterin to the subject.

4. The method of claim 1, wherein the netrin-1 is administered before, during, or after the ischemia/reperfusion injury.

5. The method of claim 1, wherein the subject is a mammalian subject.

6. The method of claim 1, wherein the subject is a human subject.

7. The method of claim 1, wherein the netrin-1 is human netrin-1.

8. The method of claim 1, wherein the administration of the netrin-1 to the subject is systemic or local administration to the heart.

9. A method of decreasing or reducing the infarct size of a heart in a subject resulting from an ischemia/reperfusion injury,
   comprising administering a therapeutically effective amount of netrin-1 to the subject, thereby decreasing or reducing the infarct size.

10. The method of claim 9 wherein netrin-1 attenuates superoxide production in the heart.

11. The method of claim 9, wherein netrin-1 attenuates NOX4 expression in the heart.

12. The method of claim 9, wherein netrin-1 reduces NOS uncoupling in the heart.

13. The method of claim 9, wherein netrin-1 increases NOS recoupling in the heart.

14. The method of claim 9, which further comprises administering sepiapterin to the subject.

15. The method of claim 9, wherein the netrin-1 is administered before, during, or after the ischemia/reperfusion injury.

16. The method of claim 9, wherein the subject is a mammalian subject.

17. The method of claim 9, wherein the subject is a human subject.

18. The method of claim 9, wherein the netrin-1 is human netrin-1.

19. The method of claim 9, wherein the administration of the netrin-1 to the subject is systemic or local administration to the heart.

\* \* \* \* \*

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Forward primer for DCC

<400> SEQUENCE: 1
cagcaaaaac tgtgcaagga                                            20

<210> SEQ ID NO 2
<211> LENGTH: 20
<212> TYPE: DNA
<213> ORGANISM: Artificial Sequence
<220> FEATURE:
<223> OTHER INFORMATION: Reverse primer for DCC

<400> SEQUENCE: 2
```
cgcaaagttc agaatcgtca                                               20

<210> SEQ ID NO 3
<211> LENGTH: 20
<212> TYPE: DNA
<213> ORGANISM: Artificial Sequence
<220> FEATURE:
<223> OTHER INFORMATION: Forward primer for UNC5B

<400> SEQUENCE: 3
agtgtaatgg cgagtgggtc                                               20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for UNC5B

<400> SEQUENCE: 4
cgaagagttc ctccacttgc                                               20

<210> SEQ ID NO 5
<211> LENGTH: 20
<212> TYPE: DNA
<213> ORGANISM: Artificial Sequence
<220> FEATURE:
<223> OTHER INFORMATION: Forward primer for Neogenin

<400> SEQUENCE: 5
tgaaccagtt gtgggaaaca                                               20

<210> SEQ ID NO 6
<211> LENGTH: 20
<212> TYPE: DNA
<213> ORGANISM: Artificial Sequence
<220> FEATURE:
<223> OTHER INFORMATION: Reverse primer for Neogenin

<400> SEQUENCE: 6
gccactcatt ggaggtttgt                                               20

<210> SEQ ID NO 7
<211> LENGTH: 20
<212> TYPE: DNA
<213> ORGANISM: Artificial Sequence
<220> FEATURE:
<223> OTHER INFORMATION: Forward primer for UNC5A

<400> SEQUENCE: 7
cgtgtcctgc acttcaaaga                                               20

<210> SEQ ID NO 8
<211> LENGTH: 20
<212> TYPE: DNA
<213> ORGANISM: Artificial Sequence
<220> FEATURE:
<223> OTHER INFORMATION: Reverse primer for UNC5A

<400> SEQUENCE: 8
cctggtagct gacaaggagc                                               20

<210> SEQ ID NO 9
<211> LENGTH: 20
<212> TYPE: DNA
<213> ORGANISM: Artificial Sequence

```
<220> FEATURE:
<223> OTHER INFORMATION: Forward primer for UNC5C

<400> SEQUENCE: 9
cacatctgga gtggctctca                                                    20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for UNC5C

<400> SEQUENCE: 10
gcatagcttc tgccggatag                                                    20

<210> SEQ ID NO 11
<211> LENGTH: 20
<212> TYPE: DNA
<213> ORGANISM: Artificial Sequence
<220> FEATURE:
<223> OTHER INFORMATION: Forward primer for UNC5D

<400> SEQUENCE: 11
gtaaagcagc tcaaggtggc                                                    20

<210> SEQ ID NO 12
<211> LENGTH: 20
<212> TYPE: DNA
<213> ORGANISM: Artificial Sequence
<220> FEATURE:
<223> OTHER INFORMATION: Reverse primer for UNC5D

<400> SEQUENCE: 12
atgcagcagc tttggttctt                                                    20

<210> SEQ ID NO 13
<211> LENGTH: 20
<212> TYPE: DNA
<213> ORGANISM: Artificial Sequence
<220> FEATURE:
<223> OTHER INFORMATION: Forward primer for Alpha 6

<400> SEQUENCE: 13
gtgtgtgaac atcaggtgcc                                                    20

<210> SEQ ID NO 14
<211> LENGTH: 20
<212> TYPE: DNA
<213> ORGANISM: Artificial Sequence
<220> FEATURE:
<223> OTHER INFORMATION: Reverse primer for Alpha 6

<400> SEQUENCE: 14
atattctgag cagcagcggt                                                    20

<210> SEQ ID NO 15
<211> LENGTH: 20
<212> TYPE: DNA
<213> ORGANISM: Artificial Sequence
<220> FEATURE:
<223> OTHER INFORMATION: Forward primer for Alpha 3

<400> SEQUENCE: 15
gctgacctga tcatctgcaa                                                    20
```

```
<210> SEQ ID NO 16
<211> LENGTH: 20
<212> TYPE: DNA
<213> ORGANISM: Artificial Sequence
<220> FEATURE:
<223> OTHER INFORMATION: Reverse primer for Alpha 3

<400> SEQUENCE: 16
gcagtaggac aggaaggcag                                                 20

<210> SEQ ID NO 17
<211> LENGTH: 20
<212> TYPE: DNA
<213> ORGANISM: Artificial Sequence
<220> FEATURE:
<223> OTHER INFORMATION: Forward primer for Beta 4

<400> SEQUENCE: 17
gagagcgaga gggtgtcatc                                                 20

<210> SEQ ID NO 18
<211> LENGTH: 20
<212> TYPE: DNA
<213> ORGANISM: Artificial Sequence
<220> FEATURE:
<223> OTHER INFORMATION: Reverse primer for Beta 4

<400> SEQUENCE: 18
atatctccat tgggcctcct                                                 20

<210> SEQ ID NO 19
<211> LENGTH: 25
<212> TYPE: RNA
<213> ORGANISM: Artificial Sequence
<220> FEATURE:
<223> OTHER INFORMATION: Sense NOX4 siRNA

<400> SEQUENCE: 19
caugcugcug cuguugcaug uuuca                                           25

<210> SEQ ID NO 20
<211> LENGTH: 25
<212> TYPE: RNA
<213> ORGANISM: Artificial Sequence
<220> FEATURE:
<223> OTHER INFORMATION: Antisense NOX4 siRNA

<400> SEQUENCE: 20
cccucugaug uaauggaacu ccgua                                           25
```